(12) United States Patent
Locke et al.

(10) Patent No.: US 11,511,032 B2
(45) Date of Patent: Nov. 29, 2022

(54) DRESSING USING DIFFERENTIAL SURFACE FEATURES FOR USE IN COMPARTMENT SPACES

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 16/979,684

(22) PCT Filed: Jan. 11, 2019

(86) PCT No.: PCT/US2019/013150
§ 371 (c)(1),
(2) Date: Sep. 10, 2020

(87) PCT Pub. No.: WO2019/177683
PCT Pub. Date: Sep. 19, 2019

(65) Prior Publication Data
US 2021/0045927 A1    Feb. 18, 2021

Related U.S. Application Data

(60) Provisional application No. 62/641,841, filed on Mar. 12, 2018.

(51) Int. Cl.
*A61M 1/00* (2006.01)
*A61F 13/00* (2006.01)
*A61F 13/02* (2006.01)

(52) U.S. Cl.
CPC ......... *A61M 1/90* (2021.05); *A61F 13/00068* (2013.01); *A61F 13/0216* (2013.01); *A61M 1/86* (2021.05); *A61M 1/915* (2021.05)

(58) Field of Classification Search
CPC .. A61M 1/90; A61M 1/732; A61M 2205/073; A61M 2205/3344;
(Continued)

(56) References Cited

U.S. PATENT DOCUMENTS 1,355,846 A    10/1920    Rannells
2,547,758 A     4/1951    Keeling
(Continued)

FOREIGN PATENT DOCUMENTS

AU    550575 B2    3/1986
AU    745271 B2    3/2002
(Continued)

OTHER PUBLICATIONS

Let's talk about PU (polyurethane) coatings; Alpine Trek.co.uk; https://www.alpinetrek.co.uk/base-camp/lets-talk-about-pu-coatings/, Published Jan. 3, 2018, Expert Guest Author (Year: 2018).*

(Continued)

*Primary Examiner* — Benjamin J Klein

(57) ABSTRACT

A dressing for treating a tissue site, particularly an abdominal or peritoneal site, is disclosed. In some embodiments, the dressing may comprise a tissue interface formed from a first layer of a liquid-impermeable material and a plurality of manifolding bubbles formed as part of the first layer. In some embodiments, the tissue interface may further comprise a second layer of a permeable material, where the manifolding bubbles are formed as closed cells between the first layer and the second layer. The tissue interface may also include a third layer of liquid-impermeable material positioned adjacent to the second layer, where one or more fluid passageways may be formed between the second layer and third layer for delivering a therapeutic fluid to the tissue site.

19 Claims, 14 Drawing Sheets

US 11,511,032 B2
Page 2

(58) Field of Classification Search
CPC ...... A61M 2205/581; A61M 2205/582; A61M 2205/583; A61M 2205/587; A61M 2205/8206; A61M 1/815; A61M 2205/3331; A61M 2205/8212; A61M 2207/10; A61M 1/74; A61M 1/915; A61F 13/00068; A61F 13/0216

See application file for complete search history.

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A * | 8/1995 | Todd .................... A61M 1/90 604/313 |
| 5,527,293 | A | 6/1996 | Zamierowski |
| 5,549,584 | A * | 8/1996 | Gross .................... A61M 1/82 604/313 |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 * | 12/2010 | Weston ................ A61F 15/008 604/313 |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 10,646,645 | B2 * | 5/2020 | Kim .................... A61M 5/16813 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2004/0073151 | A1 * | 4/2004 | Weston ............. A61F 13/00068 602/41 |
| 2007/0038172 | A1 * | 2/2007 | Zamierowski ........ A61M 27/00 604/20 |
| 2008/0300555 | A1 * | 12/2008 | Olson ............... A61F 13/00068 604/313 |
| 2010/0160877 | A1 * | 6/2010 | Kagan .................... A61M 1/90 604/319 |
| 2010/0168688 | A1 * | 7/2010 | Santora ................ A61M 3/0283 604/313 |
| 2014/0163491 | A1 | 6/2014 | Schuessler et al. |
| 2015/0080788 | A1 | 3/2015 | Blott et al. |
| 2015/0141941 | A1 * | 5/2015 | Allen ............... A61F 13/00068 604/319 |
| 2015/0148760 | A1 * | 5/2015 | Dodd ............... A61F 13/00068 604/319 |

(56) References Cited

U.S. PATENT DOCUMENTS

| | | | |
|---|---|---|---|
| 2015/0209492 A1* | 7/2015 | Blott | A61M 3/022 604/319 |
| 2016/0030646 A1* | 2/2016 | Hartwell | A61M 1/90 604/319 |

FOREIGN PATENT DOCUMENTS

| | | | | |
|---|---|---|---|---|
| AU | 755496 | B2 | 12/2002 | |
| CA | 2005436 | A1 | 6/1990 | |
| DE | 26 40 413 | A1 | 3/1978 | |
| DE | 43 06 478 | A1 | 9/1994 | |
| DE | 29 504 378 | U1 | 9/1995 | |
| EP | 0100148 | A1 | 2/1984 | |
| EP | 0117632 | A2 | 9/1984 | |
| EP | 0161865 | A2 | 11/1985 | |
| EP | 0358302 | A2 | 3/1990 | |
| EP | 1018967 | A1 | 7/2000 | |
| EP | 2815731 | A1 | 12/2014 | |
| EP | 2815731 | A1 * | 12/2014 | A61F 13/00068 |
| GB | 692578 | A | 6/1953 | |
| GB | 2195255 | A | 4/1988 | |
| GB | 2 197 789 | A | 6/1988 | |
| GB | 2 220 357 | A | 1/1990 | |
| GB | 2 235 877 | A | 3/1991 | |
| GB | 2 329 127 | A | 3/1999 | |
| GB | 2 333 965 | A | 8/1999 | |
| JP | 4129536 | B2 | 8/2008 | |
| SG | 71559 | | 4/2002 | |
| WO | 80/02182 | A1 | 10/1980 | |
| WO | 87/04626 | A1 | 8/1987 | |
| WO | 90/010424 | A1 | 9/1990 | |
| WO | 93/009727 | A1 | 5/1993 | |
| WO | 94/20041 | A1 | 9/1994 | |
| WO | 96/05873 | A1 | 2/1996 | |
| WO | 97/18007 | A1 | 5/1997 | |
| WO | 99/13793 | A1 | 3/1999 | |
| WO | 2010075179 | A2 | 7/2010 | |
| WO | WO-2010075179 | A2 * | 7/2010 | A61M 1/0023 |
| WO | 2011112724 | A1 | 9/2011 | |
| WO | 2015148636 | A1 | 10/2015 | |
| WO | WO-2015148636 | A1 * | 10/2015 | A61F 13/00068 |
| WO | 2018226627 | A1 | 12/2018 | |
| WO | 2018226669 | A1 | 12/2018 | |

OTHER PUBLICATIONS

International Search Report and Written Opinion for Corresponding Application No. PCT/US2019/013150 dated May 7, 2019.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, YU. A., et al; "Vacuum Therapy in the Treatment of Purulent Lactation Mastitis"; Vestnik Khirurgi, May 14, 1986, pp. 66-70, and 9 page English translation thereof.
Yusupov. YU.N., et al; "Active Wound Drainage", Vestnki Khirurgi, vol. 138, Issue 4, 1987, and 7 page English translation thereof.
Davydov, YU.A., et al; "Bacteriological and Cytological Assessment of Vacuum Therapy for Purulent Wounds"; Vestnik Khirugi, Oct. 1988, pp. 48-52, and 8 page English translation thereof.
Davydov, YU.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.

(56) References Cited

OTHER PUBLICATIONS

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

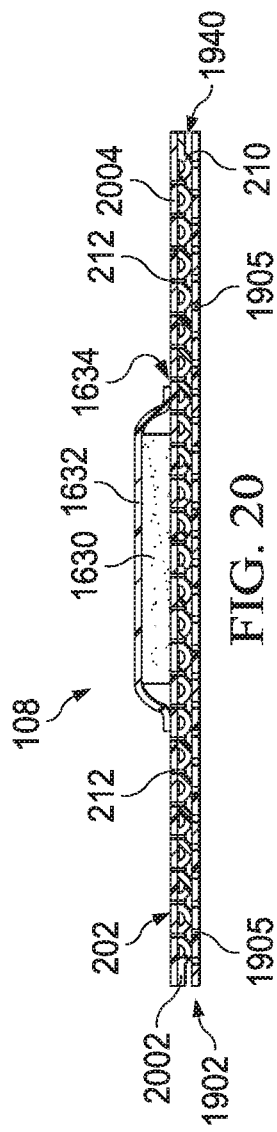 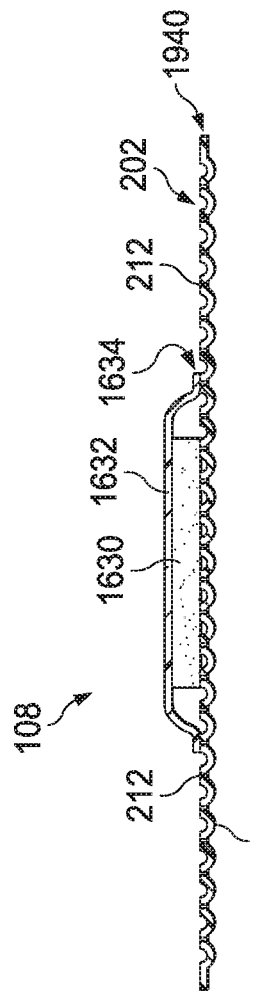 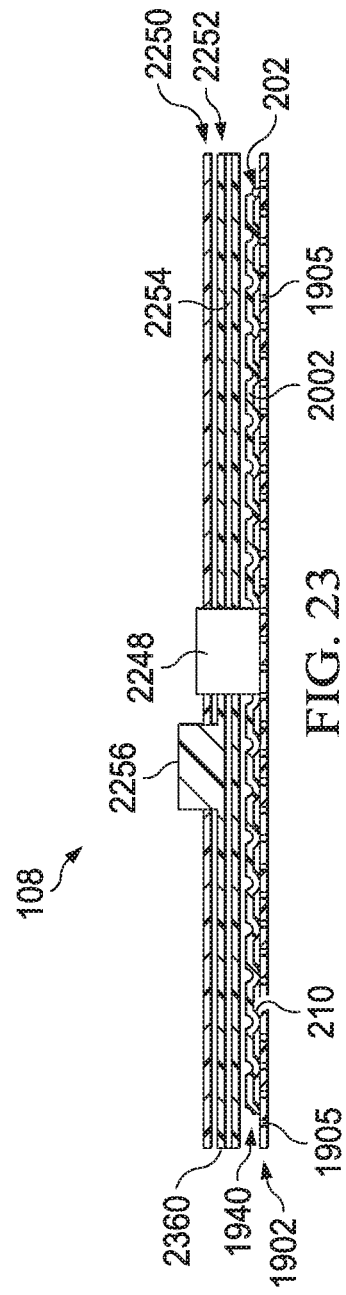

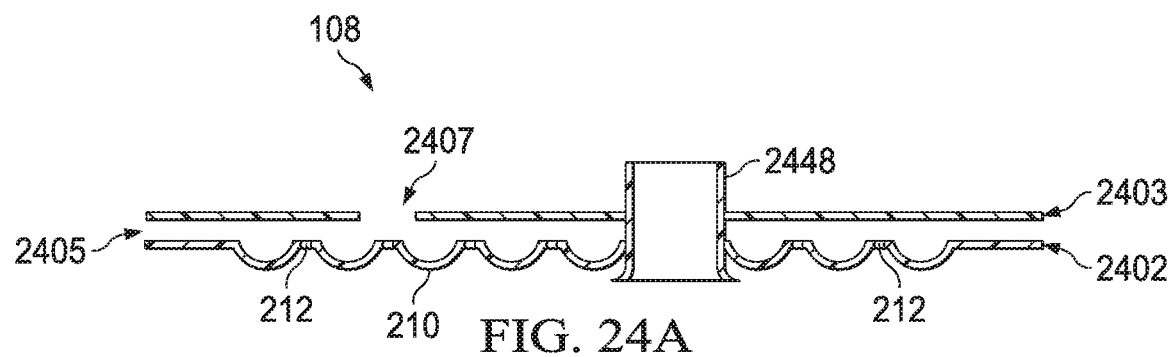
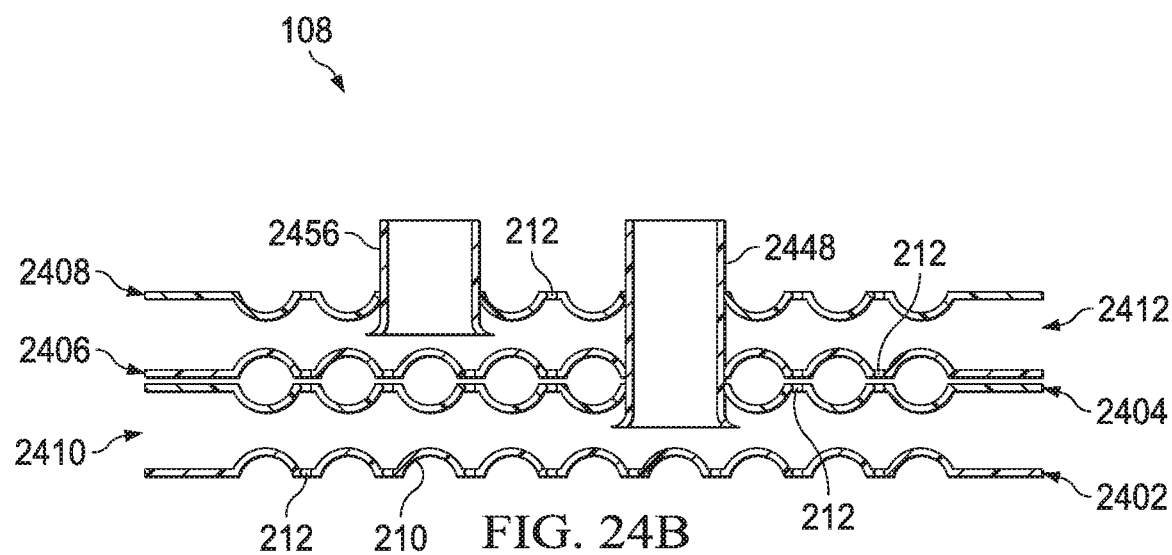

1

DRESSING USING DIFFERENTIAL SURFACE FEATURES FOR USE IN COMPARTMENT SPACES

CROSS-REFERENCE TO RELATED APPLICATIONS

This application claims the priority benefit of U.S. Provisional Application No. 62/641,841, entitled "DRESSING USING DIFFERENTIAL SURFACE FEATURES FOR USE IN COMPARTMENT SPACES," filed Mar. 12, 2018, the contents of which are incorporated herein by reference in their entirety.

TECHNICAL FIELD

The invention set forth in the appended claims relates generally to tissue treatment systems and more particularly, but without limitation, to dressings for tissue treatment and methods of using the dressings for tissue treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a system for treating an abdominal tissue site may include a tissue interface, a cover, and a negative-pressure source. The tissue interface may include a liquid-impermeable layer and a plurality of bubbles. The cover may be adapted to form a fluid seal around the tissue interface and the abdominal tissue site. The negative-pressure source may be adapted to be fluidly connected to the tissue interface. In some embodiments, the plurality of bubbles may include a plurality of blisters, and in some additional or alternative embodiments, the plurality of bubbles may include closed cells.

Additional example embodiments may include a dressing for treating an abdominal tissue site comprising a fenestrated manifold, a bubble manifold, and a foam manifold. The fenestrated manifold may include a first liquid-impermeable layer having a plurality of fenestrations, wherein the fenestrated manifold has a first side and a second side. The bubble manifold may include a second liquid-impermeable layer and a plurality of bubbles, wherein the bubble manifold has a first side and a second side. The foam manifold may be adapted to be positioned adjacent a central portion of the bubble manifold. In some embodiments, the foam manifold may comprise a foam member and a layer of liquid-impermeable material adapted to form a seal around the foam member with the bubble manifold. Additionally, in some embodiments, the bubble manifold may include a central portion and a plurality of fluid channels that extend radially away from the central portion towards a perimeter of the dressing.

A method for treating an abdominal tissue site is also described herein, wherein some example embodiments include positioning a tissue interface, covering the tissue interface and the abdominal tissue site with a drape to provide a fluid seal around the tissue interface and the abdominal tissue site, and providing negative pressure from a negative-pressure source coupled to the tissue interface and the abdominal tissue site. The tissue interface may include a first polymeric layer and a plurality of bubbles. In some embodiments, the tissue interface may further include a foam manifold member positioned against a portion of a first surface of the first polymeric layer.

In some additional embodiments, a dressing for treating a tissue site may include a first sheet of polymeric film and a second sheet of polymeric film that is substantially coextensive with the first sheet of polymeric film. The first sheet of polymeric film may comprise a first plurality of bubbles and a first plurality of apertures. The second sheet of polymeric film may comprise a second plurality of bubbles and a second plurality of apertures. A first fluid passageway may be included, which may be formed through a central portion of the first sheet of polymeric film and adapted to communicate a therapeutic fluid to a space between the first sheet of polymeric film and the second sheet of polymeric film. A second fluid passageway may also be included, which may be formed through the first sheet of polymeric film and the second sheet of polymeric film and adapted to communicate negative pressure to the tissue site.

In some further embodiments, a system for treating a tissue site may include a fenestrated manifold, a bubble manifold, and a fluid distribution matrix. The fenestrated manifold may comprise a first liquid-impermeable layer having a plurality of fenestrations, and the fenestrated manifold may have a first side and a second side. The bubble manifold may include a second liquid-impermeable layer and a plurality of bubbles formed on the second liquid-impermeable layer, and the bubble manifold may have a first side and a second side. The fluid distribution matrix may comprise a fluid distribution hub and a plurality of fluid distribution channels. Additionally, the system may further include a third liquid-impermeable layer adapted to be positioned adjacent the fluid distribution matrix in order to encapsulate the fluid distribution matrix between the fenestrated manifold and the third liquid-impermeable layer.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 20 is a section view illustrating additional details that may be associated with an example embodiment of the tissue interface of FIG. 19;

FIG. 21 is a section view illustrating additional details that may be associated with another example embodiment of the tissue interface of FIG. 19;

FIG. 23 is a section view illustrating additional details that may be associated with some example embodiments of the tissue interface of FIG. 22;

FIG. 24A is a section view of another illustrative embodiment of a tissue interface that may be associated with some embodiments of the therapy system of FIG. 1;

FIG. 24B is a section view of another illustrative embodiment of a tissue interface that may be associated with some embodiments of the therapy system of FIG. 1;

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
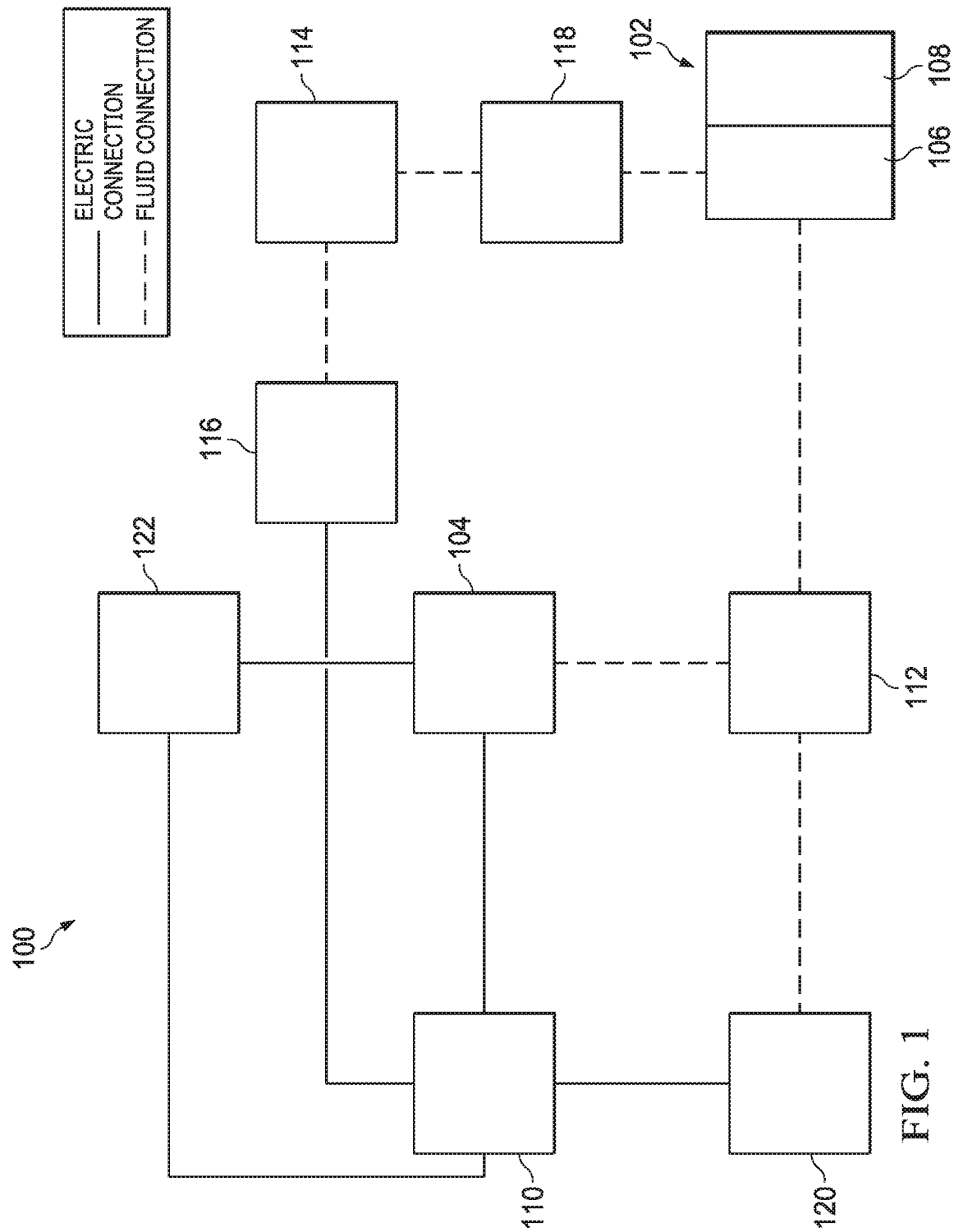
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 104, and one or more distribution components. A distribution component is preferably detachable and may be disposable, reusable, or recyclable. A dressing, such as a dressing 102, and a fluid container, such as a container 112, are examples of distribution components that may be associated with some examples of the therapy system 100. As illustrated in the example of FIG. 1, the dressing 102 may comprise or consist essentially of a tissue interface 108, a cover 106, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 102. For example, such a dressing interface may be a SENSA-T.R.A.C.™ Pad available from Kinetic Concepts, Inc. of San Antonio, Tex.

The therapy system 100 may also include a regulator or controller, such as a controller 110. Additionally, the therapy system 100 may include sensors to measure operating parameters and provide feedback signals to the controller 110 indicative of the operating parameters. As illustrated in FIG. 1, for example, the therapy system 100 may include a first sensor 120 and a second sensor 122 coupled to the controller 110.

The therapy system 100 may also include a source of instillation solution. For example, a solution source 114 may be fluidly coupled to the dressing 102, as illustrated in the example embodiment of FIG. 1. The solution source 114 may be fluidly coupled to a positive-pressure source such as a positive-pressure source 116, a negative-pressure source such as the negative-pressure source 104, or both in some embodiments. A regulator, such as an instillation regulator 118, may also be fluidly coupled to the solution source 114 and the dressing 102 to ensure proper dosage of instillation solution (e.g. saline) to a tissue site. For example, the instillation regulator 118 may comprise a piston that can be pneumatically actuated by the negative-pressure source 104 to draw instillation solution from the solution source during a negative-pressure interval and to instill the solution to a dressing during a venting interval. Additionally or alternatively, the controller 110 may be coupled to the negative-pressure source 104, the positive-pressure source 116, or both, to control dosage of instillation solution to a tissue site. In some embodiments, the instillation regulator 118 may also be fluidly coupled to the negative-pressure source 104 through the dressing 102, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110, the solution source 114, and other components into a therapy unit.

In general, components of the therapy system 100 may be coupled directly or indirectly. For example, the negative-pressure source 104 may be directly coupled to the container 112 and may be indirectly coupled to the dressing 102 through the container 112. Coupling may include fluid, mechanical, thermal, electrical, or chemical coupling (such as a chemical bond), or some combination of coupling in some contexts. For example, the negative-pressure source 104 may be electrically coupled to the controller 110 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 104, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 104 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the first sensor 120 and the second sensor 122, are generally known in the art as any apparatus operable to detect or measure a physical phenomenon or property, and generally provide a signal indicative of the phenomenon or property that is detected or measured. For example, the first sensor 120 and the second sensor 122 may be configured to measure one or more operating parameters of the therapy system 100. In some embodiments, the first sensor 120 may be a transducer configured to measure pressure in a pneumatic pathway and convert the measurement to a signal indicative of the pressure measured. In some embodiments, for example, the first sensor 120 may be a piezo-resistive strain gauge. The second sensor 122 may optionally measure operating parameters of the negative-pressure source 104, such as a voltage or current, in some embodiments. Preferably, the signals from the first sensor 120 and the second sensor 122 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The tissue interface 108 can be generally adapted to partially or fully contact a tissue site. The tissue interface 108 may take many forms, and may have many sizes, shapes, or thicknesses, depending on a variety of factors, such as the type of treatment being implemented or the nature and size of a tissue site. For example, the size and shape of the tissue interface 108 may be adapted to the contours of deep and irregular shaped tissue sites. Any or all of the surfaces of the tissue interface 108 may have an uneven, coarse, or jagged profile.

In some embodiments, the tissue interface 108 may comprise or consist essentially of a manifold. A manifold in this context may comprise or consist essentially of a means for collecting or distributing fluid across the tissue interface 108 under pressure. For example, a manifold may be adapted to receive negative pressure from a source and distribute negative pressure through multiple apertures across the tissue interface 108, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, a manifold may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of a manifold may also vary according to needs of a prescribed therapy. For example, the tensile strength of foam may be increased for instillation of topical treatment solutions. The 25% compression load deflection of the manifold may be at least 0.35 pounds per square inch, and the 65% compression load deflection may be at least 0.43 pounds per square inch. In some embodiments, the tensile strength of the manifold may be at least 10 pounds per square inch. The manifold may have a tear strength of at least 2.5 pounds per inch. In some embodiments, the manifold may be foam comprised of polyols such as polyester or polyether, isocyanate such as toluene diisocyanate, and polymerization modifiers such as amines and tin compounds. In some examples, the manifold may be reticulated polyurethane foam such as found in GRANUFOAM™ Dressing or V.A.C. VERAFLO™ Dressing, both available from Kinetic Concepts, Inc. of San Antonio, Tex.

A manifold may be either hydrophobic or hydrophilic. In an example in which a manifold is hydrophilic, the manifold may also wick fluid away from a tissue site, while continuing to distribute negative pressure to the tissue site. The wicking properties of the manifold may draw fluid away from a tissue site by capillary flow or other wicking mechanisms. An example of a hydrophilic material that may be suitable is a polyvinyl alcohol, open-cell foam such as V.A.C. WHITEFOAM™ Dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

In some embodiments, a manifold may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. A manifold may further serve as a scaffold for new cell-growth, or a scaffold material may be used in conjunction with the manifold to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may comprise or consist of, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 106 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, Calif.; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 106 may comprise INSPIRE 2301 having an MVTR (upright cup technique) of 2600 $g/m^2/24$ hours and a thickness of about 30 microns.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive configured to bond the cover 106 to epidermis around a tissue site. In some embodiments, for example, some or all of the cover 106 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 114 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 108 may be placed within, over, on, or otherwise proximate to a tissue site. If the tissue site is a wound, for example, the tissue interface 108 may partially or completely fill the wound, or it may be placed over the wound. The cover 106 may be placed over the tissue interface 108 and sealed to an attachment surface near a tissue site. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 108 in the sealed therapeutic environment can induce macro-strain and micro-strain in the tissue site. Negative pressure can also remove exudate and other fluid from a tissue site, which can be collected in container 112.

In some embodiments, the controller 110 may receive and process data from one or more sensors, such as the first sensor 120. The controller 110 may also control the operation of one or more components of the therapy system 100 to manage the pressure delivered to the tissue interface 108. In some embodiments, controller 110 may include an input for receiving a desired target pressure and may be programmed for processing data relating to the setting and inputting of the target pressure to be applied to the tissue interface 108. In some example embodiments, the target pressure may be a fixed pressure value set by an operator as the target negative pressure desired for therapy at a tissue site and then provided as input to the controller 110. The target pressure may vary from tissue site to tissue site based on the type of tissue forming a tissue site, the type of injury or wound (if any), the medical condition of the patient, and the preference of the attending physician. After selecting a desired target pressure, the controller 110 can operate the negative-pressure source 104 in one or more control modes based on the target pressure and may receive feedback from one or more sensors to maintain the target pressure at the tissue interface 108.

The controller 110 may function according to one or more control modes. In some embodiments, the controller 110 may have a continuous pressure mode, in which the negative-pressure source 104 is operated to provide a constant target negative pressure for the duration of treatment or until manually deactivated. Additionally or alternatively, the controller 110 may have an intermittent pressure mode. In some examples, the controller 110 can operate the negative-pressure source 104 to cycle between a target pressure and atmospheric pressure. For example, the target pressure may be set at a value of 135 mmHg for a specified period of time (e.g., 5 min), followed by a specified period of time (e.g., 2 min) of deactivation. The cycle can be repeated by activating the negative-pressure source 104, which can operate according to a square wave pattern between the target pressure and atmospheric pressure.

In some example embodiments, the increase in negative-pressure from ambient pressure to the target pressure may not be instantaneous. For example, the negative-pressure source 104 and the dressing 102 may have an initial rise time. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time may be a value substantially equal to the initial rise time.

According to another example pressure control mode, such as a dynamic pressure mode, the target pressure can vary with time. For example, the target pressure may vary in the form of a triangular waveform, varying between a negative pressure of 50 and 135 mmHg with a rise time set at a rate of +25 mmHg/min. and a descent time set at −25 mmHg/min. In other embodiments of the therapy system 100, the triangular waveform may vary between negative pressure of 25 and 135 mmHg with a rise time set at a rate of +30 mmHg/min and a descent time set at −30 mmHg/min.

In some embodiments, the controller 110 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 110, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 2:
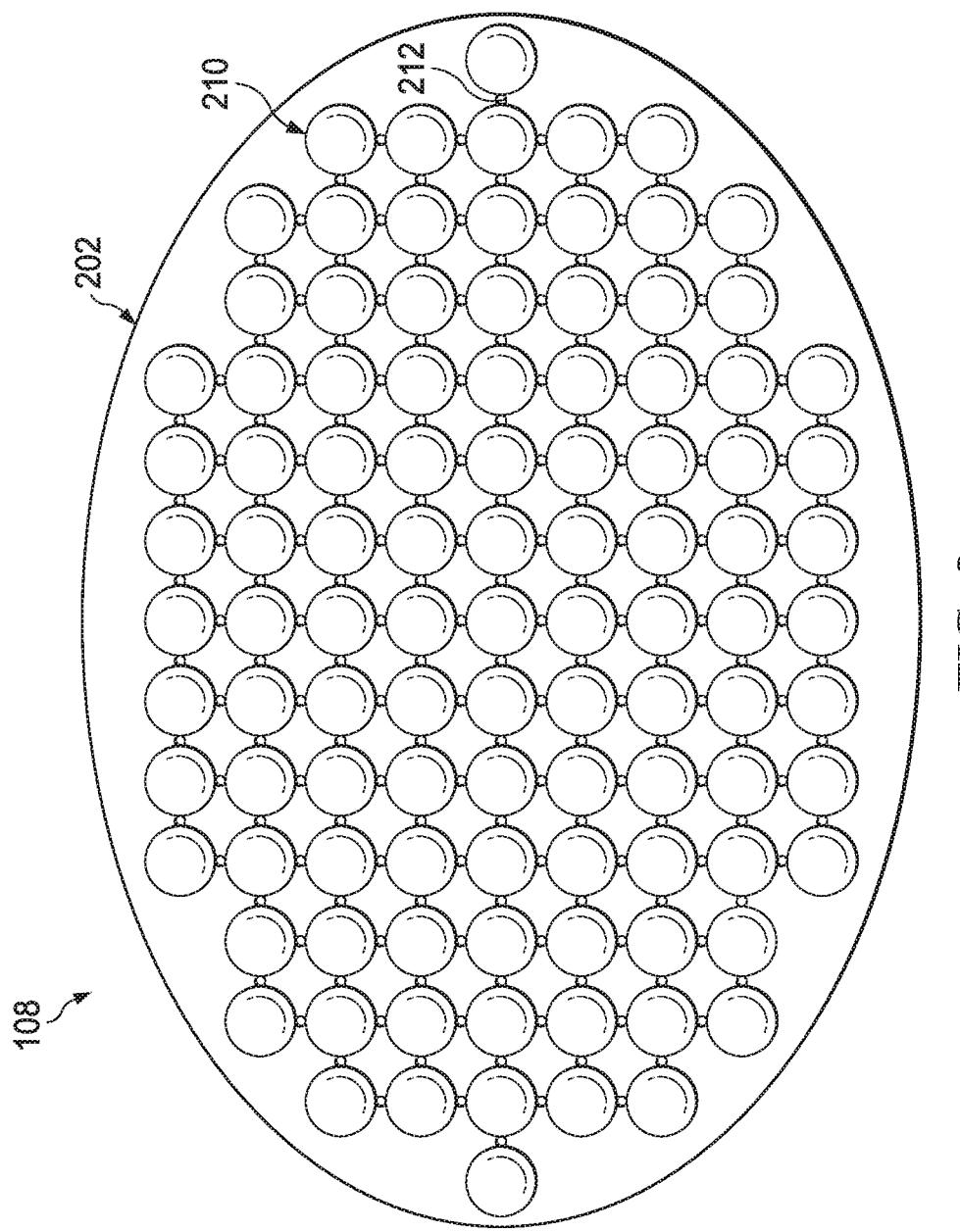
FIG. 2 is a schematic, plan view of an illustrative embodiment of a tissue interface that may be associated with some embodiments of the therapy system of FIG. 1.

FIG. 2 is a schematic top-view of an example of the tissue interface 108, illustrating additional details that may be associated with some embodiments. The tissue interface 108 generally comprises or consists essentially of a manifold or a manifold layer. The tissue interface 108 may be adapted to provide negative pressure from the negative-pressure source 104 of the therapy system 100 to a tissue site, and to collect and transport fluid extracted from the tissue site. For example, the tissue interface 108 may be adapted to receive negative pressure from the negative-pressure source 104 and distribute the negative pressure through multiple apertures across the tissue interface 108, which may have the effect of collecting fluid from across a tissue site and drawing the fluid toward the negative-pressure source 104. In some embodiments, the fluid path may be reversed or a secondary fluid path may be provided to facilitate delivering fluid, such as from a source of instillation solution, across the tissue interface 108. The tissue interface 108 may comprise a bubble manifold 202, which may include a plurality of bubbles 210. The bubbles 210 may be in the form of open-celled blisters, spacers, protrusions, or other raised formations. In some additional embodiments, the bubbles 210 may be in the form of closed cells. Each of the plurality of bubbles 210 may comprise a substantially circular, oval, triangular, square, or other shape, as appropriate. In some instances, triangular-shaped bubbles may maintain their height longer under compression, such as under the application of negative pressure within an abdominal space. Furthermore, the bubbles 210 may be textured, or include surface texture features. The bubble manifold 202 of the tissue interface 108 may additionally comprise apertures 212 positioned between the bubbles 210 to allow fluid transfer through the bubble manifold 202. In some embodiments, the apertures 212 may comprise perforations or fenestrations.

Figure 3:
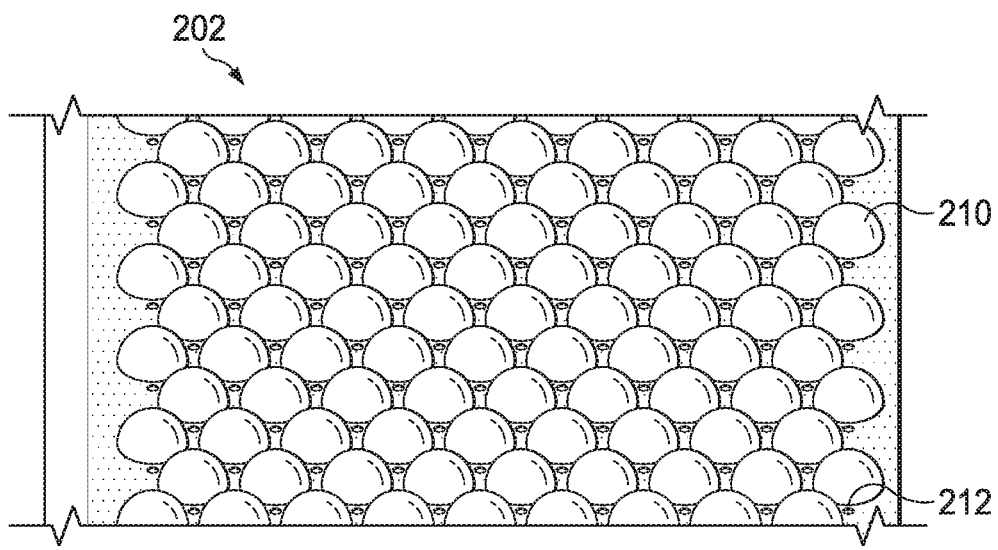
FIG. 3 is a top view of an example configuration of a bubble manifold that may be included in some embodiments of the tissue interface of FIG. 2.

FIG. 3 is a perspective view of an example of the bubble manifold 202 of FIG. 2, illustrating additional details that may be associated with some embodiments. As illustrated in the example of FIG. 3, the bubbles 210 may be in the form of blisters, and may be generally hemispherical and uniformly distributed in some embodiments. For example, the bubble manifold 202 may comprise or consist essentially of a film of liquid-impermeable material, such as a polyurethane material, having bubbles 210 in the form of blisters. In some embodiments, the blisters may comprise a plurality of raised formations that extend above or below a plane of the bubble manifold 202. Within each of the blisters may be an empty cavity which may be open to the surrounding environment. For example, portions of a film of liquid-impermeable material that forms the bubble manifold 202 may be shaped or formed into the blisters. In some embodiments, the blisters may be in the form of small vacuum-formed regions of the film of the bubble manifold 202.

The bubbles 210 may have dimensions that depend on the particular application of the bubble manifold 202 and tissue interface 108. For example, the bubbles 210 may be in the form of blisters having a height between approximately 1.0 mm and 4.0 mm and may have a diameter between approximately 1.0 mm and 4.0 mm. In some embodiments, the blisters may measure approximately 1.5 mm in height and approximately 1.5 mm in diameter. The distance between each of the blisters may be between approximately 1.0 mm and 3.0 mm, and in some embodiments may have a spacing of approximately 2.0 mm. In some embodiments, each individual blister may be dome-shaped or hemispherically-shaped. Additionally or alternatively, the blisters may be in the form of raised formations having different shapes, such as generally conical, cylindrical, tubular having a flattened or hemispherical end, or geodesic. Furthermore, the bubbles 210 may vary in size or spacing across a surface area of the bubble manifold 202. For example, the bubbles 210 may be smaller or larger in a central portion of the bubble manifold 202, and/or may gradually decrease or increase in size along a distance from a central portion to perimeter portion of the bubble manifold 202. For example, the bubbles 210 may be larger towards a perimeter portion of the bubble manifold 202, which may have the effect of mitigating potential pressure drops across the bubble manifold 202. Additionally, the bubbles 210 may be increasingly spaced further apart or more closely along a distance from a central portion to a perimeter portion of the bubble manifold 202. The shape of the bubbles 210 may also change along a distance from a central portion to a perimeter portion of the bubble manifold 202. Such variations in size, spacing/density, and shape may aid with deploying the bubble manifold 202 and tissue interface 108 to establish an appropriate fluid removal gradient at a tissue site.

The thickness of the bubble manifold 202 may also vary according to the needs of a prescribed therapy. For example, the thickness of the bubble manifold 202 may be decreased to relieve stress or tension on tissue at a tissue site. The thickness of the bubble manifold 202 can also affect the conformability of the tissue interface 108. In some embodiments, the bubble manifold 202 may comprise a film having a material thickness in a range of about 20 to 500 micrometers, or in some more specific embodiments in a range of about 50 to 150 micrometers. Depending on the particular embodiment, the orientation of the bubble manifold 202 may be reversed so that the bubbles 210 of the bubble manifold 202 may either face or extend upwards or downwards from a plane of the bubble manifold 202.

The bubble manifold 202 may additionally include apertures 212 positioned between the bubbles 210 to allow fluid transfer through the film of the bubble manifold 202. The number of apertures 212 may vary depending on the type of negative pressure and/or instillation therapy to be provided by the therapy system 100. The apertures 212 may have different shapes and sizes, and the apertures 212 may have a diameter, major axis, or length between about 0.5 mm and 1.5 mm. The apertures 212 may be fenestrations, in some embodiments. In some embodiments, the bubble manifold 202 may comprise a polyurethane film with vacuum-formed blisters that is subsequently fenestrated with slits. Additionally, the bubble manifold 202 may be formed with rings, which may be in the form of concentric circles, in regions of the bubble manifold 202 between areas of the bubble manifold 202 comprising bubbles 210. The rings may provide a visual cue to a user to aid with sizing of the tissue interface 108, which may include cutting. In some embodiments, the rings of the bubble manifold 202 may be formed during a vacuum-forming process of the bubble manifold 202, and may include weakened regions or designated areas of the bubble manifold 202 for cutting or otherwise sizing. For example, if the vacuum draw corresponding to the regions of the bubble manifold 202 where the rings are desired is higher than the vacuum applied to surrounding areas of the bubble manifold 202, weaknesses would be formed in desired areas that would allow for preferential tearing or cutting.

Figure 4:
FIG. 4 is a section view illustrating additional details that may be associated with some embodiments of the bubble manifold of FIG. 3.

FIG. 4 is a section view of an example embodiment of the bubble manifold 202 of FIG. 3, illustrating additional details that may be associated with some embodiments. For example, the bubble manifold 202 may be formed of a single sheet or film of liquid-impermeable material, which may have the bubbles 210 and apertures 212 formed thereon. In some embodiments, the bubbles 210 may be in the form of blisters and may be formed in the bubble manifold 202 by applying a vacuum to the film of liquid-impermeable material of the bubble manifold 202 to create the blisters.

As shown in FIG. 4, the apertures 212 may be formed in the portions of the bubble manifold 202 that are between the bubbles 210 and may extend through the film of liquid-impermeable material to permit fluids to flow through the bubble manifold 202. The number of apertures 212 may vary depending on the type of negative pressure and instillation therapy to be provided by the therapy system 100. The apertures 212 may have different shapes, such as, for example, circular, elliptical, rectangular, or other irregular shape. Such apertures 212 may have a diameter, major axis, or length between about 0.5 mm and 1.5 mm. In some example embodiments, the apertures 212 may be formed by cutting or perforating the liquid-impermeable material of the bubble manifold 202.

Figure 5:
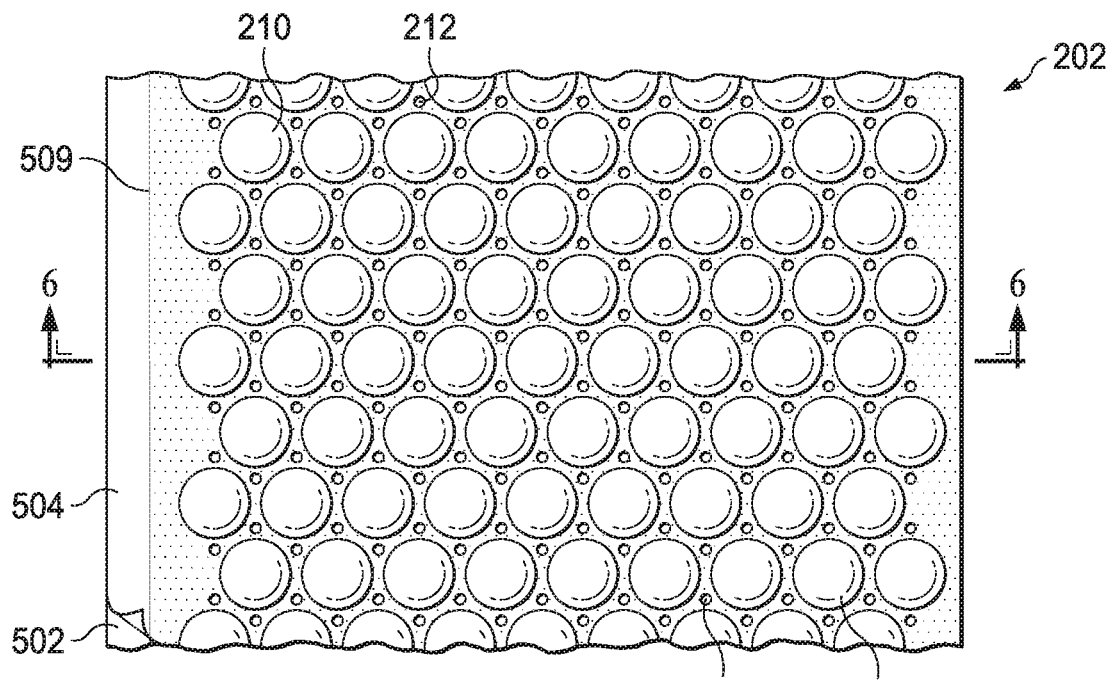
FIG. 5 is a top view of an example configuration of a bubble manifold that may be included in some additional embodiments of the tissue interface of FIG. 2.

FIG. 5 is a perspective view of a portion of another example of the bubble manifold 202 of FIG. 2, illustrating additional details that may be associated with some embodiments. In some embodiments, the bubble manifold 202 may comprise a manifold and may be formed with a plurality of liquid-impermeable layers, e.g., a first layer 502 and a second layer 504. "Liquid impermeable" with respect to "liquid-impermeable layers" means that the layers are formed with a liquid-impermeable material. Thus, although formed with a liquid-impermeable material, the first layer 502 and the second layer 504 may be liquid permeable when fenestrated, perforated, or otherwise include fluid passageways, but nonetheless are referred to as liquid-impermeable layers. In some embodiments, the first layer 502 and the second layer 504 may be sealingly coupled to one another in any suitable manner, such as, without limitation, by welding, bonding, adhesives, cements, or other bonding devices. In some embodiments, the first layer 502 and the second layer 504 may comprise a non-adherent material, such as a medical drape, capable of inhibiting tissue from adhering to the medical drape. For example, in some embodiments, the first layer 502 and the second layer 504 may comprise a liquid-impermeable polymeric film, such as a breathable polyurethane film.

In some embodiments, each of the first layer 502 and the second layer 504 may comprise or consist essentially of a liquid-impermeable polymer film, having inner surfaces coupled to each other to form a sealed region 509 defining a plurality of bubbles 210, which may be in the form of closed cells. The inner surfaces of the first layer 502 and the second layer 504 may be coupled to each other to form bubbles 210 that are in the form of closed cells that are substantially airtight to inhibit excessive collapsing of the bubbles 210 from the application of negative pressure, which could block the flow of fluid through or along the bubble manifold 202.

The two sheets of liquid-impermeable, polymeric film, first layer 502 and second layer 504, may be in the form of a single sheet of material having two laminae or two separate sheets that are coupled together to form the bubbles 210. The sheets of liquid-impermeable, polymeric film may initially be separate sheets that are brought into superposition and sealed or they may be formed by folding a single sheet unto itself with a heat sealable surface facing inward. Each sheet of the liquid-impermeable polymeric film also may be a monolayer or multilayer structure depending on the application of the desired structure of the bubbles 210.

The sheets of liquid-impermeable, polymeric film may comprise any flexible material that can be manipulated to enclose the bubbles 210 formed of closed cells. For example, the bubble manifold 202 may be formed of two welded layers of polyolefin film that encapsulates air in pockets. Additionally or alternatively, various thermoplastic materials may be used for producing the film layers of the bubble manifold 202. Non-limiting examples of suitable thermoplastic polymers include polyethylene homopolymers, such as low density polyethylene (LDPE) and high density polyethylene (HDPE), and polyethylene copolymers, such as, ionomers, EVA, EMA, heterogeneous (Zeigler-Natta catalyzed) ethylene/alpha-olefin copolymers, and homogeneous (metallocene, single-cite catalyzed) ethylene/alpha-olefin copolymers. Ethylene/alpha-olefin copolymers are copolymers of ethylene with one or more comonomers selected from $C_3$ to $C_{20}$ alpha-olefins, such as 1-butene, 1-pentene, 1-hexene, 1-octene, and methyl pentene, in which the polymer molecules comprise long chains with relatively few side chain branches, including linear low-density polyethylene (LLDPE), linear medium-density polyethylene (LMDPE), very low-density polyethylene (VLDPE), and ultra-low-density polyethylene (ULDPE). Various other materials are also suitable such as, polypropylene homopolymer or polypropylene copolymer (e.g., propylene/ethylene copolymer), polyesters, polystyrenes, polyamides, polycarbonates, etc.

The bubbles 210 formed of closed cells may be preferably resistant to collapsing under therapeutic levels of negative pressure. In some embodiments, the bubbles 210 may be formed by a material having sufficient tensile strength to resist stretching under apposition forces of negative pressure. The tensile strength of a material is the ability of material to resist stretching as represented by a stress-strain curve, where stress is the force per unit area, i.e., pascals (Pa), newtons per square meter (N/m²), or pounds per square inch (psi). The ultimate tensile strength (UTS) is the maximum stress the material can withstand while being stretched before failing or breaking. Many materials display a linear elastic behavior defined by a linear stress-strain relationship often extending up to a nonlinear region represented by the yield point, i.e., the yield strength of a material. For example, high-density polyethylene (HDPE) has a high tensile strength and low-density polyethylene (LDPE) has a slightly lower tensile strength, both of which are suitable materials for forming the bubbles 210. Linear low-density polyethylene (LLDPE) may be used as well because the material stretches very little as the force is increased up to the yield point of the material. The yield strength of HDPE ranges from 26-33 MPa, and has a UTS of 37 MPa, while LDPE has somewhat lower values. In some example embodiments, the bubbles 210 may be formed from a material that has a yield strength greater than about 20 MPa.

In some example embodiments, the sealed region 509 may be formed by a heat seal between the inner surfaces of the first layer 502 and the second layer 504. Additionally or alternatively, the sealed region 509 may be formed by adhesion between the first layer 502 and the second layer 504. The first layer 502 and the second layer 504 may also be adhesively bonded to each other. The bubbles 210 may be substantially airtight closed cells when formed and have an internal pressure that is substantially an ambient pressure. In other embodiments, the bubbles 210 may be closed cells that are inflated with air or other suitable gas, such as, for example, carbon dioxide or nitrogen. The bubbles 210 may be closed cells that are inflated to have an internal pressure greater than the atmospheric pressure to maintain their shape and resistance to collapsing under pressure. For example, the bubbles 210 may be inflated to a pressure up to about 25 psi above the atmospheric pressure so that they do not collapse.

The sealed region 509 comprises sealed segments between the bubbles 210 that may be flexible enough so that the bubble manifold 202 is sufficiently flexible to conform to the shape of the tissue site. The sealed segments may be sufficiently flexible or sized so that the bubble manifold 202 may be folded into two or more layers. The sealed segments of the sealed region 509 may serve as common boundaries between adjacent bubbles 210. The sealed segments of the sealed region 509 may also be perforated to provide pathways for fluid to flow through the bubble manifold 202. In some example embodiments, the sealed region 509 may include a plurality of apertures 212 between the bubbles 210 in the sealed region 509 and extending through both the first layer 502 and the second layer 504 to permit fluid to flow through the bubble manifold 202. The number of apertures 212 may vary depending on the type of negative pressure and instillation therapy to be provided by the therapy system 100. The apertures 212 may have different shapes, such as, for example, circular, elliptical, rectangular, or other irregular shape. Such apertures 212 may have a diameter, major axis, or length between about 0.5 mm and 1.5 mm. In other example embodiments, the apertures 212 may be formed by perforating or cutting the segments of the sealed region 509.

As illustrated in the example of FIG. 5, the sealed region 509 may define the base or the cross-sectional shape of each of the bubbles 210 as generally circular. Additionally or alternatively, the base of one or more of the bubbles 210 may have other shapes, such as rectangular, triangular, or hexagonal. The bubbles 210 may be formed with a three-dimensional shape corresponding to the cross-sectional shape of the bubbles 210. For example, the volumetric shape may be generally hemispherical or spherical in shape as shown. In other embodiments, the bubbles 210 may be formed with a volumetric shape that is generally conical, cylindrical, tubular having a flattened or hemispherical end, or geodesic shape. The bubbles 210 that are generally hemispherical or spherical in shape may have a diameter between about 0.5 mm and 10 mm. The bubbles 210 also may have a pitch, i.e., the center to center distance between each of the bubbles 210, between about 1.5 mm and 15 mm. Because the sealed region 509 defines the base of the bubbles 210 including the diameter of a circular base and the pitch of adjacent bubbles 210, the surface area of the bubble manifold 202 covered by the bubbles 210 may also be determined as a percentage, i.e., the cell coverage percentage. In one example embodiment where the diameter of the bubbles 210 is about 1.0 mm and the pitch is about 2.0 mm, the bubble coverage is about 22% of the surface area of the bubble manifold 202. In another example embodiment where the diameter of the bubbles 210 is about 2.0 mm and the pitch is about 5.0 mm, the bubble coverage percentage is about 14% of the surface area of the bubble manifold 202. In yet another example embodiment where the diameter of the bubbles 210 is about 1.0 mm and the pitch is about 1.5 mm, the bubble coverage percentage is about 30% of the surface area of the bubble manifold 202. In still another example embodiment where the diameter of the bubbles 210 is about 1.5 mm, the pitch is about 2.0 mm, and the bubbles 210 are more tightly arranged such that there are about 28.5 bubbles in a 10 mm² section of the bubble manifold 202, the bubble coverage percentage is about 51% of the surface area of the bubble manifold 202. Depending on the diameter, pitch, and arrangement of the bubbles 210, the bubble coverage percentage may range between about 10% and about 55% of the surface area of the bubble manifold 202. Bubbles 210 having other base shapes or volumetric shapes also may have a bubble coverage percentage in generally the same range.

Some embodiments of the bubbles 210 may have three-dimensional shapes, including hemispherical shapes, spherical shapes, conical shapes, cylindrical shapes, or tubular shapes formed with a flattened or hemispherical end. These shapes may be formed in one or both of the first layer 502 and the second layer 504, such as the single hemispherical shape shown in FIG. 6 (bubbles 210) and the two hemispherical shapes that are aligned with one another to form a spherical shape as shown in FIG. 7 (bubbles 210). The bubbles 210 may have a height between about 0.25 mm and about 5 mm, e.g., about half the diameter of bubbles 210 having a hemispherical shape as described in the examples above. In some embodiments, the bubbles 210 may measure about 10 mm in diameter and about 3 mm in height. In other example embodiments, the bubbles 210 may have a generally tubular shape formed with generally parallel walls extending from the sealed region 509 to a hemispherical end. In yet other example embodiments, bubbles 210 having a tubular shape may have a diameter of about 1.5 mm and an average height in a range between about 2.0 mm and 4.0 mm.

Still referring primarily to FIG. 5, the first layer 502 and the second layer 504 may each have a thickness of about 5 µm to 500 µm, and the sealed region 509 may be between about 10 µm and 1000 µm in thickness. The walls of the bubbles 210, after being formed by coupling the first layer 502 and the second layer 504 together, may have a thickness relative to the thickness of the first layer 502 and the second layer 504 defined by a draw ratio, which is the ratio of the average height of the bubbles 210 to the average thickness of the first layer 502 and the second layer 504. In one example embodiment where the bubbles 210 have a generally tubular shape, the first layer 502 and the second layer 504 may have an average thickness of 250 μm and the bubbles 210 may have an average height in a range between about 2.0 mm and 4.0 mm with a diameter of about 1.5 mm. Consequently, the bubbles 210 have a draw ratio ranging from about 8:1 to about 16:1 for heights of 2.0 mm and 4.0 mm, respectively. In another example embodiment, the first layer 502 and the second layer 504 may have an average thickness of 100 μm and the bubbles 210 may have an average height in a range between about 2.0 mm and 4.0 mm with a diameter of about 1.5 mm. Consequently, the bubbles 210 have a draw ratio ranging from about 20:1 to about 40:1 for heights of 2.0 mm and 4.0 mm, respectively. In yet other example embodiments, it is desirable that the draw ratio be greater than about 16:1 where the thickness of the first layer 502 and the second layer 504 is less than about 250 μm. The first layer 502 and the second layer 504 may each have the same thickness or different thicknesses and flexibilities, but are substantially non-stretchable as desired above so that the bubbles 210 maintain a generally constant volume without bursting after negative pressure or instillation fluid is applied to the bubble manifold 202. Consequently, even when a load is applied to the bubble manifold 202 which squeezes bubbles 210 into a different shape, the bubbles 210 are sufficiently flexible to recover their original shape after being squeezed without bursting.

Figure 6:
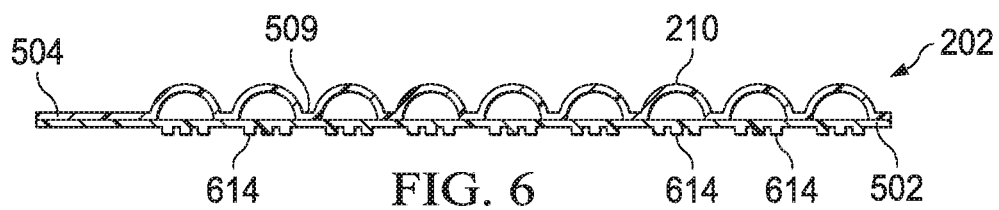
FIG. 6 is a section view illustrating additional details that may be associated with some embodiments of the bubble manifold of FIG. 5.
Figure 7:
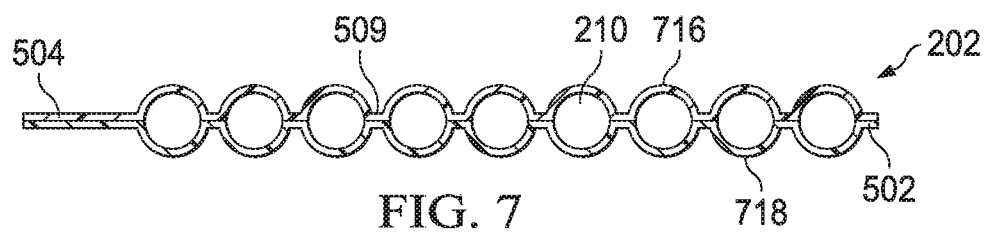
FIG. 7 is a section view illustrating details that may be associated with some additional embodiments of the bubble manifold of FIG. 5.

FIG. 6 is a section view of an example embodiment of the bubble manifold 202 of FIG. 5, illustrating additional details that may be associated with some embodiments. For example, the bubble manifold 202 of FIG. 6 may be configured so that closed cells extend from only one side of the sealed region 509 of the bubble manifold 202, such as bubbles 210 formed of closed cells having a hemispherical shape. More specifically, the bubble manifold 202 may comprise two sheets of polymeric film, such a first layer 502 and a second layer 504, having inner surfaces coupled to each other in a pattern defining a plurality of bubbles 210. The first layer 502 and the second layer 504 may be sealed to each other in a sealed region 509 that defines the bubbles 210 that are generally hemispherical in shape. The bubbles 210 may be formed on only one side of the sealed region 509 by using sheets of polymeric film having a different thickness or flexibility. For example, the bubbles 210 may be formed in the second layer 504 by applying a vacuum to the second layer 504 where the first layer 502 is sufficiently thicker than the second layer 504 to withstand the vacuum being applied and retain a generally planar shape. The bubbles 210 having other shapes may be formed to extend from only one side of the sealed region 509 and may be formed by using a variety of different methods. For example, the shape of the bubbles 210 may be formed separately in the second layer 504, which can be subsequently coupled to the first layer 502 to complete the encapsulation of the bubbles 210. The first layer 502 may have the same thickness as the second layer 504 so that the sealed region 509 remains thin and flexible.

Still referring primarily to FIG. 6, in some embodiments, the bubble manifold 202 may further include textured surface features on one or more surfaces of either or both of the first layer 502 and the second layer 504. The textured surface features may be included on a surface of either or both of the first layer 502 and the second layer 504 that may be placed facing the tissue site. The textured surface features may be protrusions or indentations for enhancing fluid flow through the bubble manifold 202 and to increase micro-strains against the tissue site for enhancing granulation. More specifically, the textured surface features may include a pattern of individual nodes or projections embossed on the outer surface of the first layer 502 and/or second layer 504, a grid embossed on the outer surface of the first layer 502 and/or second layer 504, a pattern or grid of grooves formed into the outer surface of the first layer 502 and/or second layer 504, or any combination of the foregoing. For example, as shown in FIG. 6, the bubble manifold 202 may include textured surface features in the form of nodes 614, which may be embossed on the outer surface of the first layer 502 so that the nodes 614 contact the tissue site when the bubble manifold 202 is positioned at the tissue site.

The nodes 614 may be projections that are flexible or rigid. In some embodiments, the projections may be formed from a substantially gas-impermeable material such as silicone. In other embodiments, the projections may be formed from a semi-gas-permeable material. The projections may be formed as an integral part of the first layer 502 and the second layer 504, and they may also be formed from the same material as the first layer 502 and the second layer 504. In some embodiments, the projections may be solid, while in other embodiments, the projections may be hollow to increase flexibility. The projections may form a plurality of channels and/or voids as described below to distribute negative pressure and allow for fluid flow among the projections. The projections may be dimensioned to provide local load points at a tissue site sufficient to create microstrains at the tissue site for stimulating granulation formation when negative pressure is applied. The pattern and position of the projections may be uniform or non-uniform. The projections may have different shapes including, for example, the shape of a spike, cone, pyramid, dome, cylinder, or rectangle. The shapes of the projections may be uniform or non-uniform depending on the tissue site. The shapes of the projections may occupy a volume defined by a cube volume where the side of the cube would range from approximately 0.2 mm to approximately 1.5 mm. In one embodiment, the spike shape may have a base width or diameter of about 0.2 mm and a vertical height of between about 0.4 mm and 0.8 mm. In another embodiment, the cone shape may have a base diameter of about 0.4 mm and a vertical height of between 0.4 mm and 1.2 mm. In yet another embodiment, the dome shape may have a spherical cap or parabolic shape with a base diameter ranging from about 0.4 mm to 1 mm.

FIG. 7 is a section view of another example of the bubble manifold 202 of FIG. 5, illustrating additional details that may be associated with some embodiments. For example, the bubble manifold 202 of FIG. 7 may include bubbles 210 comprising portions of closed cells that are formed in both of the two sheets or layers of the bubble manifold 202, so that the portions of bubbles 210 extend from both sides of the sealed region of the bubble manifold 202. More specifically, the bubble manifold 202 may comprise two sheets of polymeric film, first layer 502 and second layer 504, having inner surfaces coupled to each other in a pattern defining a plurality of bubbles 210. For example, the portions of bubbles 210 formed in each of the first layer 502 and the second layer 504 may each be hemispherical in shape, such as hemispherical cell 716 and hemispherical cell 718. The hemispherical cell 716 and hemispherical cell 718 may then be aligned to form a single bubble 210 in the form of a closed cell having a generally spherical shape. In other words, each of the single bubbles 210 comprises two hemispherical cells, hemispherical cell 716 and hemispherical cell 718, formed in the second layer 504 and the first layer 502, respectively. The first layer 502 and the second layer 504 may be sealed to each other in a sealed region 509 that defines the bubbles 210 that are generally spherical in shape. In other example embodiments, the closed cells in each sheet may not be aligned with each other, but rather are overlapped or aligned with the sealed portion of the opposite sheet. The bubbles 210 may be formed on both sides of the sealed region 509 by using sheets of polymeric film having a different thickness or flexibility. For example, the shape of the bubbles 210 may be asymmetric when the first layer 502 and the second layer 504 have different thicknesses or flexibilities from each other. However, when the first layer 502 and the second layer 504 have substantially identical thickness or flexibility, the shape of the bubbles 210 may be substantially spherical, as shown in FIG. 7.

Figure 8:
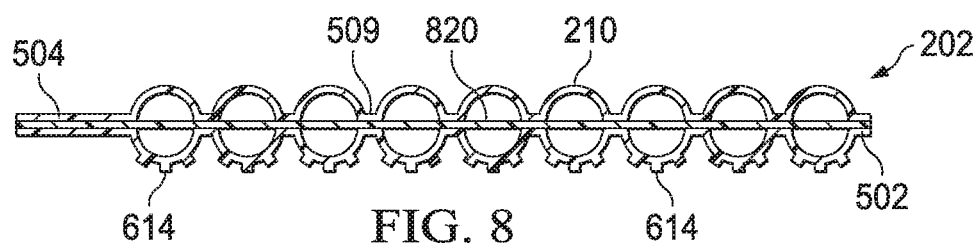
FIG. 8 is a section view illustrating details that may be associated with some additional embodiments of the bubble manifold of FIG. 5.

FIG. 8 is a section view of another example of the bubble manifold 202 of FIG. 5, illustrating additional details that may be associated with some embodiments. For example, the bubble manifold 202 of FIG. 8 may include a third sheet forming a multi-sheet configuration where the third sheet is disposed between a first sheet and a second sheet to form closed cells that may be generally spherical in shape formed by two hemispherical sections separated by portions of the third sheet of material. For example, the bubble manifold 202 of FIG. 8 may include a first layer 502 and a second layer 504 of polymeric film having inner surfaces coupled or bonded to a third layer 820 to form sealed region 509 defining a plurality of bubbles 210 in the form of closed cells. The bubbles 210 are generally spherical in shape and formed by two hemispherical sections that are separated by portions of the third layer 820. The first layer 502 and the second layer 504 may be coupled or bonded to the third layer 820 using a variety of different methods including, for example, melting (e.g., RF, ultrasonic, and heat), adhesives using both hot melt and solvents, and pressing techniques. The third layer 820 may be formed from a polymeric film and may also be perforated to permit airflow between the two hemispherical sections of the bubbles 210. When the third layer 820 is formed from a polymeric material, the third layer 820 may also be textured to provide wicking capability. The third layer 820 may also be formed from a polyester material to provide wicking within the bubbles 210 and may further include fibers flocked into the polyester material to provide additional wicking capability. The third layer 820 may also include an antimicrobial layer or antimicrobials coated on the third layer 820.

In some embodiments, the bubble manifold 202 of FIG. 8 may also include textured surface features on one or more surfaces of either or both of the first layer 502 and the second layer 504. The textured surface features may be protrusions or indentations, as discussed with respect to the textured surface features of FIG. 6. For example, the bubble manifold 202 may include projections or nodes 614 embossed on the outer surface of the first layer 502 and, more specifically, on the surface of the bubbles 210 so that the nodes 614 contact the tissue site if the bubble manifold 202 is positioned at the tissue site.

Figure 9:
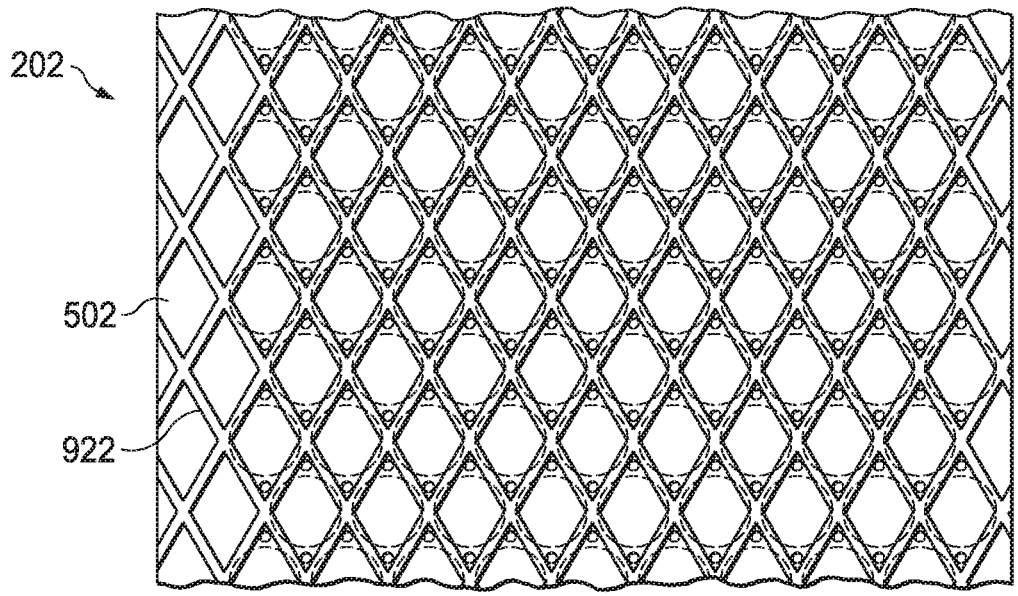
FIG. 9 is a top view of another example configuration of a bubble manifold that may be included in some additional embodiments of the tissue interface of FIG. 2.

FIG. 9 is a schematic view of a portion of another example of the bubble manifold 202 of FIG. 2, illustrating additional details that may be associated with some embodiments. For example, a number of different textures or shapes may be formed on the outside surface of a first layer 502 that may be flat and may be for facing a tissue site when in use. In one exemplary embodiment, a grid 922 may be embossed or extruded in a woven pattern on the outer surface of the first layer 502. The pattern of the grid 922 may have a variety of shapes, like the diamond-shaped pattern shown. It should be understood that many types of protrusions or grids may be formed on a surface of the first layer 502 or a first sheet of other disclosed embodiments of the bubble manifold 202 for enhancing fluid flow through or along the bubble manifold 202 and/or enhance granulation of a tissue site. Moreover, it should be understood that any of such protrusions or grids may be formed by embossing, welding, or any other similar type of coupling mechanism.

Figure 10:
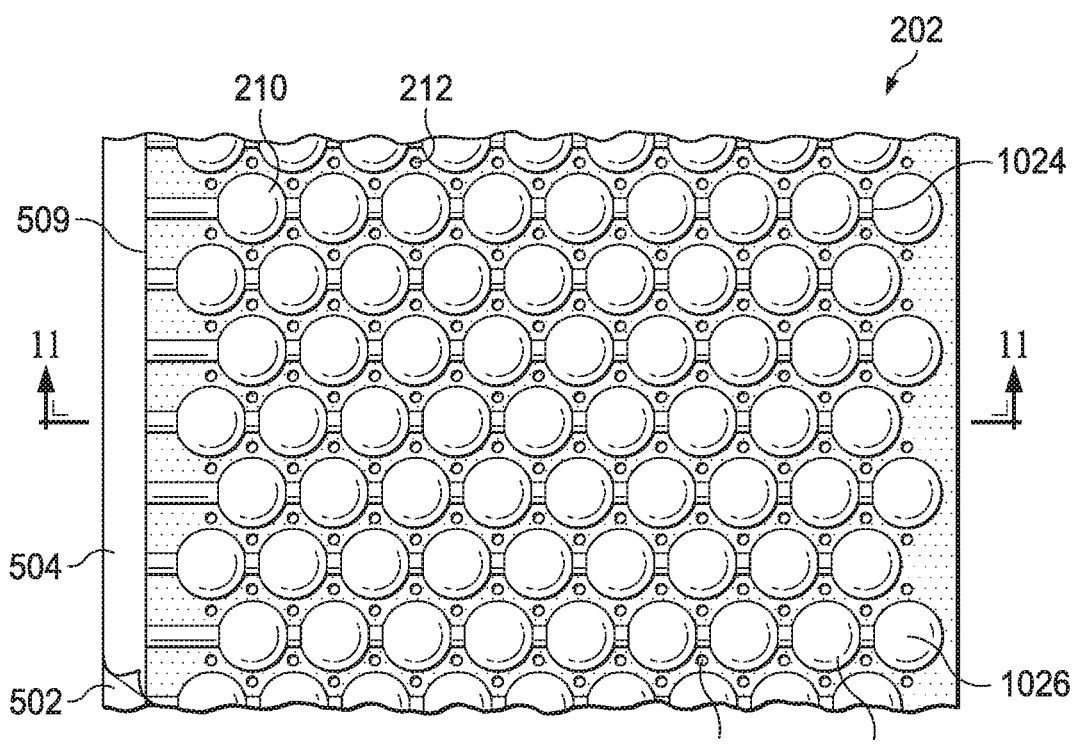
FIG. 10 is a top view of another example configuration of a bubble manifold that may be associated with some additional embodiments of the tissue interface of FIG. 2.

FIG. 10 is a schematic view of a portion of another example of the bubble manifold 202 of FIG. 2, illustrating additional details that may be associated with some embodiments. The bubble manifold 202 may be similar to the embodiments of the bubble manifold 202 previously discussed but may further include chambers formed by interconnected closed cells to better distribute the apposition force applied to the bubble manifold 202 as a result of the application of negative pressure since the volume of the chambers is greater than the volume of the individual closed cells. In one embodiment, as shown in FIG. 10, the bubble manifold 202 includes a first layer 502 and a second layer 504, each of which may be a polymeric film having inner surfaces coupled to each other in a pattern forming a sealed region 509 defining a plurality of bubbles 210 comprising closed cells. The sealed region 509 may also be perforated to provide pathways for fluid to flow through the bubble manifold 202. In one exemplary embodiment, the sealed region 509 may comprise a plurality of apertures 212 that are formed between the bubbles 210 in the sealed region 509 that extend through both of the first layer 502 and the second layer 504 to permit fluid flow through the bubble manifold 202. The bubble manifold 202 may also comprise a plurality of passageways 1024 fluidly coupling at least two of the bubbles 210 to form a closed chamber. In one exemplary embodiment, a closed chamber 1026 is formed by all of the bubbles 210 in a row fluidly coupled by the passageways 1024 as shown in FIG. 10. Closed chambers 1026 may be formed in each of the other six rows as also shown in FIG. 10. The formation of closed chambers with closed cells in any pattern may distribute apposition forces applied to the bubble manifold 202 more equally across the bubble manifold 202.

Figure 11:
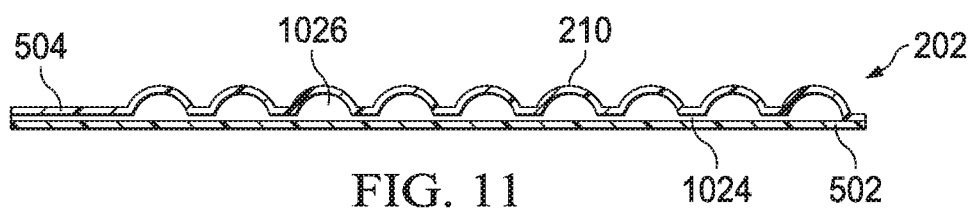
FIG. 11 is a section view illustrating additional details that may be associated with some embodiments of the bubble manifold of FIG. 10.

FIG. 11 is a section view of an example embodiment of the bubble manifold 202 of FIG. 10, illustrating additional details that may be associated with some embodiments. For example, the bubble manifold 202 of FIG. 11 may include two sheets of polymeric film, first layer 502 and second layer 504, having inner surfaces coupled to each other in a pattern defining a plurality of bubbles 210 comprising closed cells. The first layer 502 and the second layer 504 may be sealed to each other in a sealed region that defines the bubbles 210 that are generally hemispherical in shape. The bubble manifold 202 also may comprise a plurality of passageways 1024 interconnecting the bubbles 210 to form a closed chamber 1026. The closed chamber 1026 may be formed in only one of the first layer 502 and the second layer 504 so that they extend from only one side of the sealed region, as shown in FIG. 11.

Figure 12:
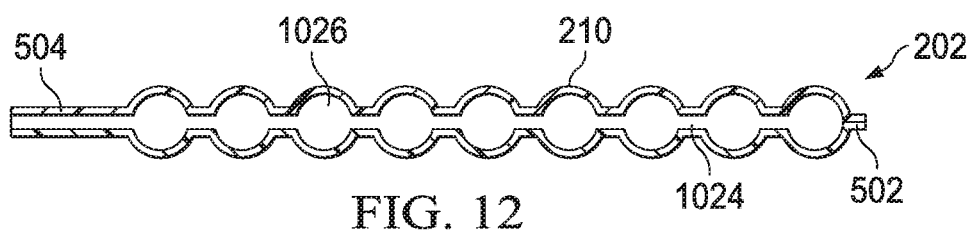
FIG. 12 is a section view illustrating details that may be associated with some additional embodiments of the bubble manifold of FIG. 10.

FIG. 12 is a section view of another example of the bubble manifold 202 of FIG. 10, illustrating additional details that may be associated with some embodiments. For example, the bubble manifold 202 of FIG. 12 may include two sheets of polymeric film, the first layer 502 and the second layer 504, having inner surfaces coupled to each other in a pattern defining a plurality of bubbles 210 comprising closed cells. The first layer 502 and the second layer 504 may be sealed to each other in a sealed region that defines the bubbles 210 that are generally spherical in shape. The bubble manifold 202 also may comprise a plurality of passageways 1024 interconnecting the bubbles 210 to form a closed chamber 1026. The closed chamber 1026 is formed in both of the first layer 502 and the second layer 504 so that they extend from both sides of the sealed region that provides more flexibility and cushioning than the closed chamber 1026 of FIG. 11 extending from only one side of the sealed region.

Figure 13:
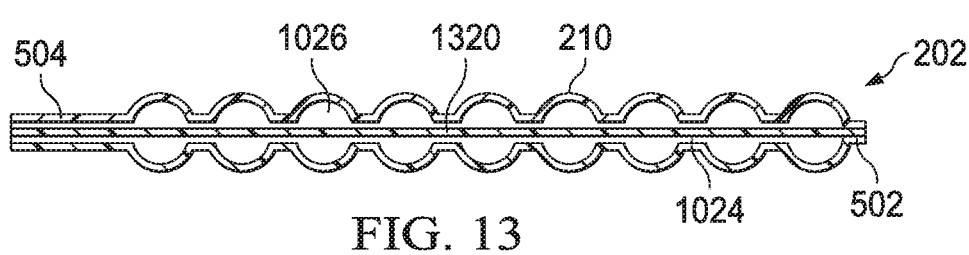
FIG. 13 is a section view illustrating details that may be associated with some additional embodiments of the bubble manifold of FIG. 10.

FIG. 13 is a section view of another example of the bubble manifold 202 of FIG. 10, illustrating additional details that may be associated with some embodiments. For example, the bubble manifold 202 of FIG. 13 may include two sheets of polymeric film, first layer 502 and second layer 504, having inner surfaces coupled or bonded to a third layer 1320 to form a sealed region defining a plurality of bubbles 210 comprising closed cells. The bubbles 210 are generally spherical in shape and formed by two hemispherical sections that are separated by portions of the third layer 1320. The first layer 502 and the second layer 504 may be coupled or bonded to the third layer 1320 using a variety of different methods including, for example, melting (e.g., RF, ultrasonic, and heat), adhesives using both hot melt and solvents, and pressing techniques. The third layer 1320 may be formed from a polymeric film and may also be perforated to permit airflow between the two hemispherical sections of the bubbles 210. When the third layer 1320 is formed from a polymeric material, the third layer 1320 may also be textured to provide wicking capability. The third layer 1320 may also be formed from a polyester material to provide wicking within the bubbles 210, and may further include fibers flocked into the polyester material to provide additional wicking capability. The third layer 1320 also may include an antimicrobial layer or antimicrobials coated on the third layer 1320. The third layer 1320 of FIG. 13 may also provide a plurality of passageways 1024 interconnecting the bubbles 210 to form a closed chamber 1026. The closed chamber 1026 of FIG. 13 is formed in both of the first layer 502 and the second layer 504 so that they extend from both sides of the sealed region.

Figure 14:
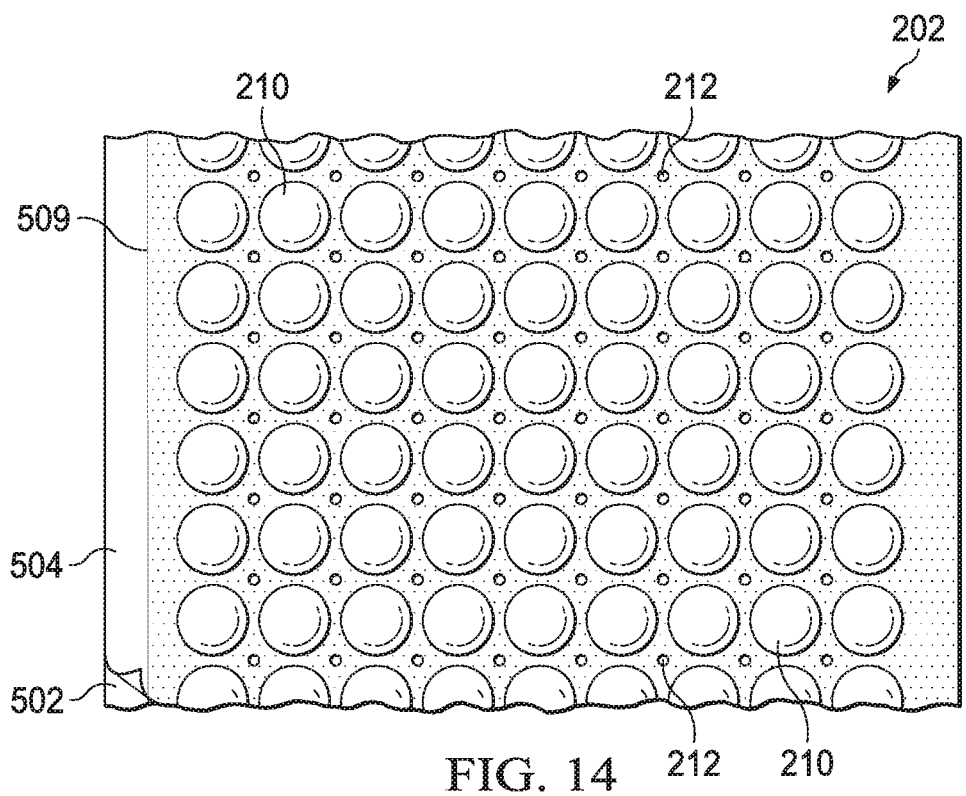
FIG. 14 is a top view of another example configuration of a bubble manifold that may be associated with some additional embodiments of the tissue interface of FIG. 2.

FIG. 14 is a schematic view of a portion of another example of the bubble manifold 202 of FIG. 2, illustrating additional details that may be associated with some embodiments. The bubble manifold 202 may be similar to the embodiments of the bubble manifold 202 previously discussed but may include different arrangements of bubbles 210 comprising closed cells, which may be suitable for particular forms of therapy being utilized. Previously discussed with respect to FIG. 5 were bubbles 210 comprising closed cells which are in a staggered arrangement so that the individual cells may be more closely nested together between the alternating rows to form a nested pattern of cells formed on the same plane as defined by the sealed region 509. FIG. 14 depicts a bubble manifold 202 that may include two sheets of polymeric film, first layer 502 and second layer 504, having inner surfaces sealed to each other in a pattern defining a plurality of bubbles 210 comprising closed cells in close proximity to one another. However, the rows and columns of bubbles 210 of FIG. 14 are not staggered, but rather arranged in an aligned pattern. Depending on the diameter and pitch of the bubbles 210, the cell coverage percentage may range between about 10% and about 55% of the surface area of the bubble manifold 202. The first layer 502 and second layer 504 may be sealed to each other in a sealed region 509 that defines the bubbles 210. In this embodiment, the rows and columns of the bubbles 210 are arranged in line to form an aligned pattern. The bubble manifold 202 may also include a sealed region 509 that may be perforated as described above. In some embodiments, the sealed region 509 may include a plurality of apertures 212 between the bubbles 210 and extending through both the first layer 502 and the second layer 504 to permit fluid to flow through the bubble manifold 202. The apertures 212 may have similar dimensions as apertures 212 of FIG. 5. The pattern of bubbles 210 may have a variety of arrangements.

Figure 15:
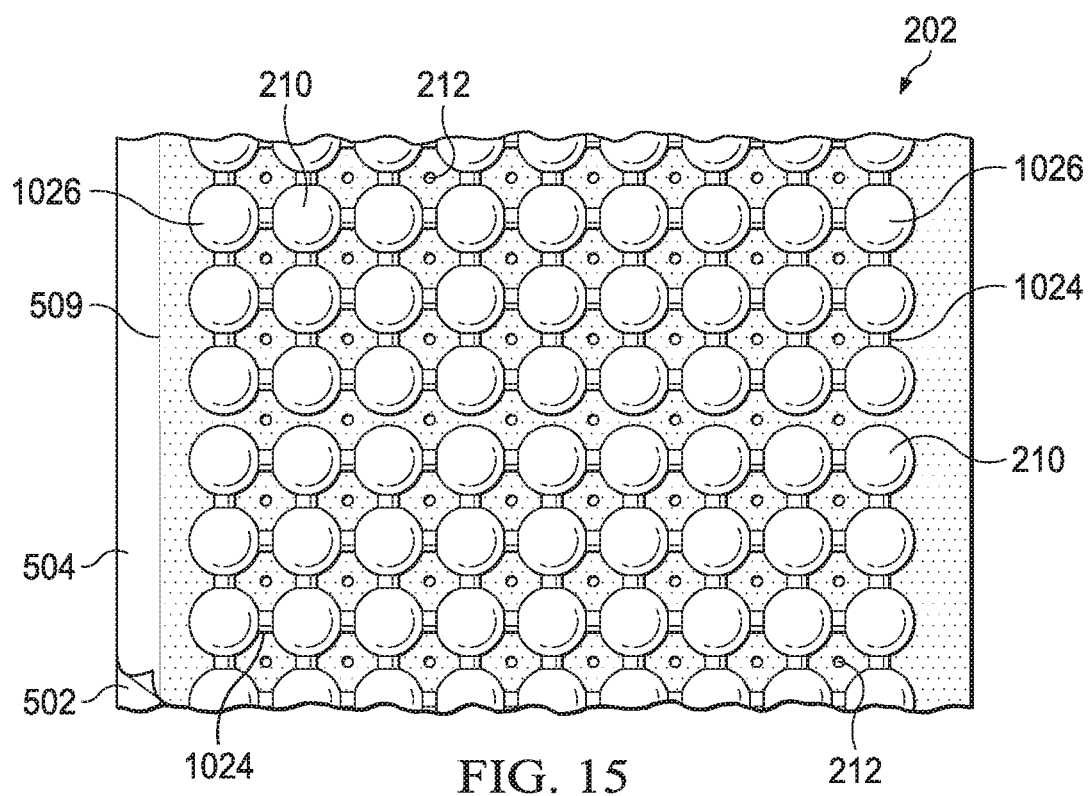
FIG. 15 is a top view of another example configuration of a bubble manifold that may be associated with some additional embodiments of the tissue interface of FIG. 2.

FIG. 15 is a schematic view of a portion of another example of the bubble manifold 202 of FIG. 2, illustrating additional details that may be associated with some embodiments. The bubble manifold 202 may be similar to the bubble manifold 202 of FIG. 14 and may include two sheets of polymeric film, first layer 502 and second layer 504, having inner surfaces sealed to each other in a pattern defining a plurality of bubbles 210 comprising closed cells in close proximity to one another. The first layer 502 and the second layer 504 may be sealed to each other in a sealed region 509 that defines the bubbles 210. The sealed region 509 may also be perforated to provide pathways for fluid to flow through the bubble manifold 202. In one exemplary embodiment, the sealed region 509 may comprise a plurality of apertures 212 that are formed between the bubbles 210 in the sealed region 509 that extend through both of the first layer 502 and the second layer 504 to permit fluid flow through the bubble manifold 202. The bubble manifold 202 may also comprise a plurality of passageways 1024 interconnecting the bubbles 210 to form a closed chamber 1026. In one exemplary embodiment, a closed chamber 1026 is formed by all of the bubbles 210 in a row fluidly coupled by the passageways 1024 as shown in FIG. 15. Closed chambers 1026 may be formed in each of the other six rows, or formed to include multiple rows, as also shown in FIG. 15. The formation of closed chambers 1026 with bubbles 210 in any pattern may distribute apposition forces applied to the bubble manifold 202 more equally across the bubble manifold 202 as opposed to a layer having only closed cells.

Figure 16:
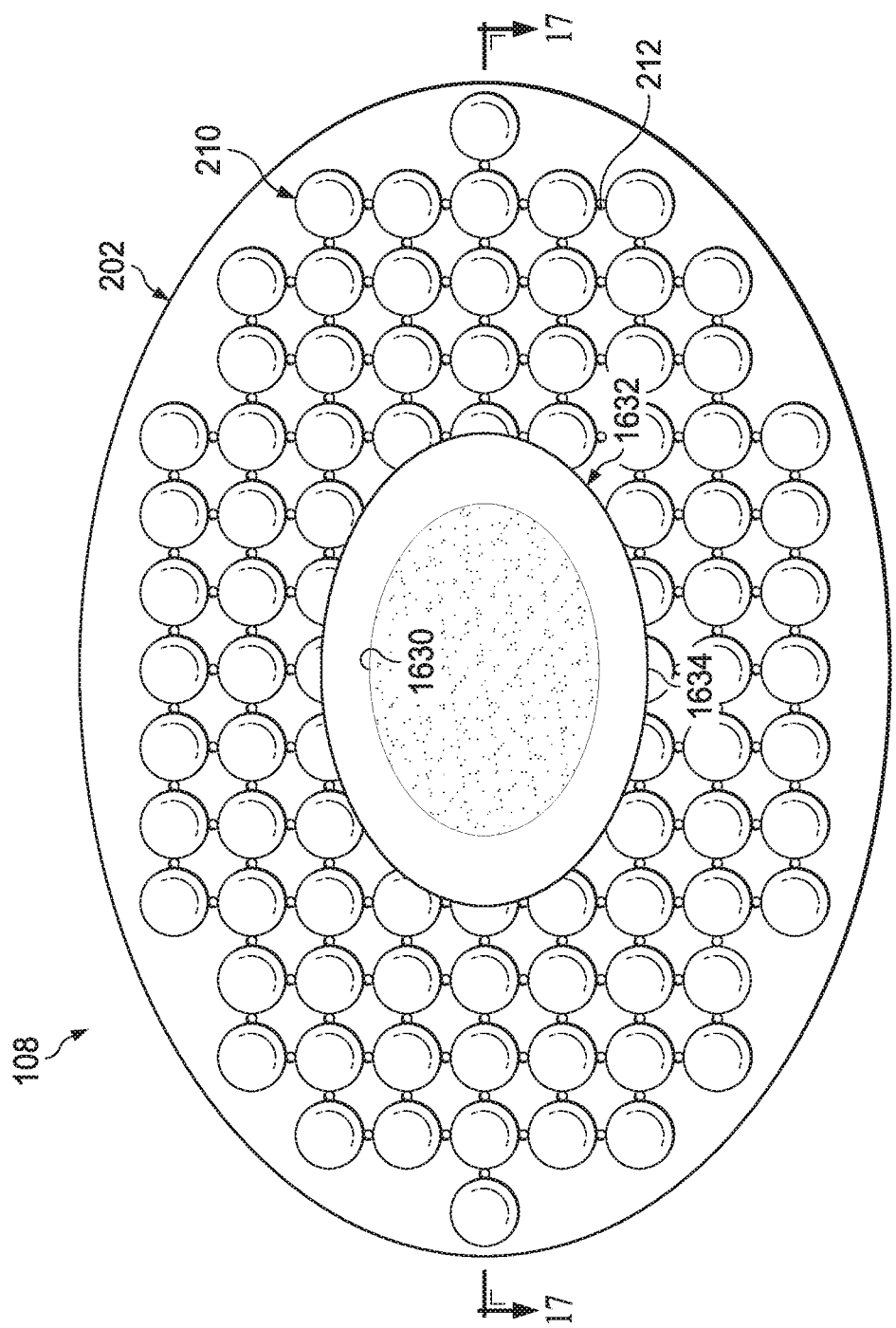
FIG. 16 is a schematic, plan view of another illustrative embodiment of a tissue interface that may be associated with some additional embodiments of the therapy system of FIG. 1.

FIG. 16 is a schematic top-view of another example of a tissue interface 108, illustrating additional details that may be associated with some embodiments. For example, the tissue interface 108 of FIG. 16 may comprise a manifold and may be adapted to provide negative pressure from the negative-pressure source 104 of the therapy system 100 to a tissue site, and to transport fluid extracted from the tissue site. The tissue interface 108 may comprise a bubble manifold 202 and a foam manifold 1630. The bubble manifold 202 may comprise a layer of liquid-impermeable material having a plurality of bubbles 210, which may be in the form of open-celled blisters, spacers, protrusions, or closed cells. The bubble manifold 202 of the tissue interface 108 of FIG. 16 may additionally comprise apertures 212 positioned between the bubbles 210 to allow fluid transfer through the bubble manifold 202 and tissue interface 108.

The tissue interface 108 of FIG. 16 may also comprise foam manifold 1630, which may include a portion of manifolding or filler material positioned in a central portion of the tissue interface 108. For example, the tissue interface 108 may include the foam manifold 1630, which may be positioned adjacent a central portion of a surface of the bubble manifold 202 of the tissue interface 108. As shown in FIG. 16, the foam manifold 1630 may have a circular or disc shape; however, other embodiments of the tissue interface 108 may also include a foam manifold 1630 of a variety of shapes, such as square or box shapes, triangular or pyramidal shapes, or any other suitable shape or configuration. In some alternative embodiments, the foam manifold 1630 may be positioned against a center region of the bubble manifold 202 that includes at least one film of liquid-impermeable material, but does not include bubbles.

The foam manifold 1630 may include one or more types of manifolding materials. For example, the foam manifold 1630 may be a porous material having interconnected fluid pathways. Examples of suitable porous material that can be adapted to form interconnected fluid pathways (e.g., channels) may include cellular foam, including open-cell foam such as reticulated foam, as well as other porous material such as gauze or felted mat that generally include pores. Liquids, gels, and other foams may also include or be cured to include apertures and fluid pathways. In some examples, the foam manifold 1630 may be reticulated polyurethane foam such as found in GRANUFOAM™ Dressing or V.A.C. VERAFLO™ Dressing, both available from Kinetic Concepts, Inc. of San Antonio, Tex.

In some embodiments, the tissue interface 108 of FIG. 16 may further include a film material, such as film 1632, for positioning over the foam manifold 1630. The film 1632 may comprise any type of film material, such as any of the suitable non-porous or liquid-impermeable polymeric or drape materials. The film 1632 may further include a plurality of fenestrations, which may be suited for allowing fluid communication between a space external to the tissue interface 108 and the foam manifold 1630. In some embodiments, the film 1632 may be sealed around the foam manifold 1630 via a weld 1634 between the film 1632 and a surface of the bubble manifold 202 surrounding a perimeter or circumference of the foam manifold 1630.

Figure 17:
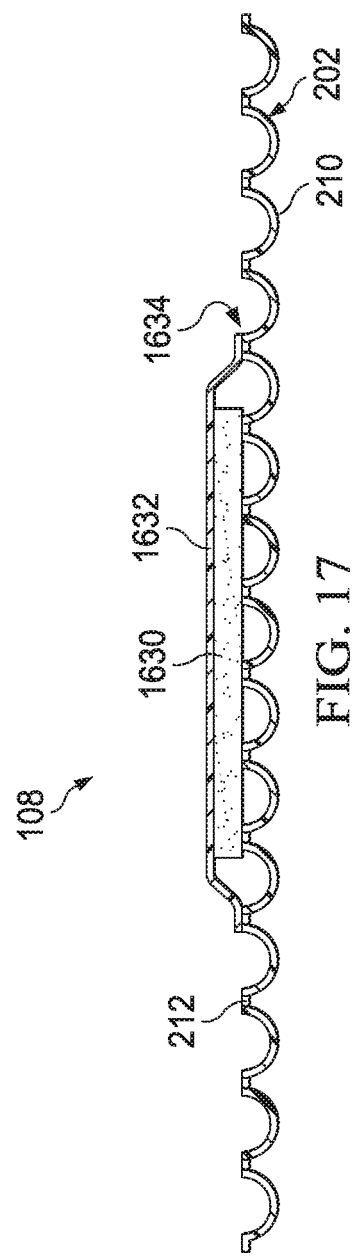
FIG. 17 is a section view illustrating additional details that may be associated with some embodiments of the tissue interface of FIG. 16.

FIG. 17 is a section view of an example embodiment of the tissue interface 108 of FIG. 16, illustrating additional details that may be associated with some embodiments. For example, the tissue interface 108 may include bubble manifold 202, which may be formed of a single sheet or film of liquid-impermeable material comprising bubbles 210 and apertures 212 formed thereon. In some embodiments, the bubbles 210 may be in the form of blisters according to the principles previously discussed. As shown in FIG. 17, the apertures 212 may be formed in the portions of the bubble manifold 202 that are between the bubbles 210 and may extend through the bubble manifold 202 to permit fluids to flow through the tissue interface 108. The number of apertures 212 may vary depending on the type of negative pressure and instillation therapy to be provided by the therapy system 100. The foam manifold 1630 may be placed on a surface of the bubble manifold 202, with the film 1632 applied over and around the foam manifold 1630. The film 1632 may be welded to a surface of the bubble manifold 202 via weld 1634. As shown in FIG. 17, the bubble manifold 202 may be positioned so that the bubbles 210, which may be in the form of blisters, protrude, extend, or face downward so as configured to face a tissue site. However, in alternative embodiments, the bubble manifold 202 may be reversed, so that the bubbles 210 extend or face upwards towards the foam manifold 1630.

Figure 18:
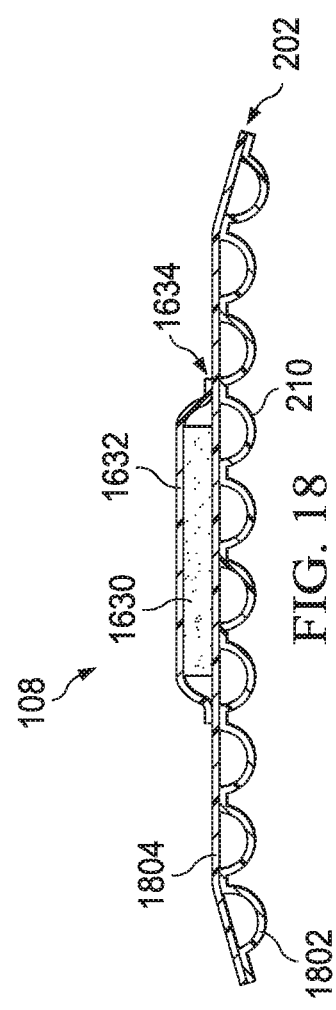
FIG. 18 is a section view illustrating additional details that may be associated with some embodiments of the tissue interface of FIG. 16.

FIG. 18 shows a section view of another example embodiment of the tissue interface 108 of FIG. 16, illustrating some additional details. For example, the tissue interface 108 of FIG. 18 may comprise a bubble manifold 202, which may be formed from a plurality of liquid-impermeable layers. The tissue interface 108 of FIG. 18 may also comprise foam manifold 1630. In some embodiments, the bubble manifold 202 of the tissue interface 108 of FIG. 18 may include a first layer of liquid-impermeable film, first layer 1802, and a second layer of liquid-impermeable film, second layer 1804. First layer 1802 and second layer 1804 may be sealingly coupled to one another in any suitable manner. As previously discussed with respect to other embodiments, the first layer 1802 and the second layer 1804 may comprise a non-adherent material, such as a breathable polyurethane film material.

The bubble manifold 202 of the tissue interface 108 of FIG. 18 may include a plurality of bubbles 210, which may be in the form of closed cells. For example, the bubbles 210 may comprise closed cells formed between the first layer 1802 and the second layer 1804 and may be filled with fluid such as air. Similar to embodiments previously discussed, each of the first layer 1802 and the second layer 1804 may have inner surfaces coupled to each other to form a sealed region defining a plurality of closed cells forming the bubbles 210. In the example embodiment of the tissue interface 108 of FIG. 18, the bubbles 210 may be formed between a majority or substantially all of the surface areas of the inner surfaces of the first layer 1802 and the second layer 1804. The bubble manifold 202 may additionally comprise apertures through the first layer 1802 and the second layer 1804, and between the bubbles 210, to allow fluid transfer through the bubble manifold 202 of the tissue interface 108.

As shown in FIG. 18, the tissue interface 108 may be configured so that the bubbles 210 comprising closed cells extend from only one side of the bubble manifold 202, which in this instance may be configured to face a tissue site. The bubbles 210 of FIG. 18 are shown with the first layer 1802 of the bubble manifold 202 forming hemispherical-shaped closed cells and the second layer 1804 of the bubble manifold 202 retaining a generally planar shape.

The tissue interface 108 of FIG. 18 may also include a portion of manifolding or filler material positioned in a central portion of the tissue interface 108. For example, the tissue interface 108 may include foam manifold 1630, which may be positioned adjacent a central portion of an external surface of the second layer 1804 of the bubble manifold 202. In some alternative embodiments, the foam manifold 1630 may be positioned in a center region of the tissue interface 108 that includes portions of the first layer 1802 and second layer 1804 of the bubble manifold 202, but does not include bubbles. In such embodiments, a center portion of the first layer 1802 and second layer 1804 of the bubble manifold 202 corresponding to the foam manifold 1630 may have inner surfaces sealed to each other, without any bubbles between the first layer 1802 and second layer 1804.

In some embodiments, the tissue interface 108 of FIG. 18 may further include a film material, such as film 1632, for positioning over the foam manifold 1630. For example, the foam manifold 1630 may be positioned between an external surface of the second layer 1804 of the bubble manifold 202 and the film 1632. The film 1632 may further include a plurality of fenestrations. The film 1632 may be sealed around the foam manifold 1630 via a weld 1634 between the film 1632 and an external surface of the second layer 1804 of the bubble manifold 202 surrounding a perimeter or circumference of the foam manifold 1630.

Figure 19:
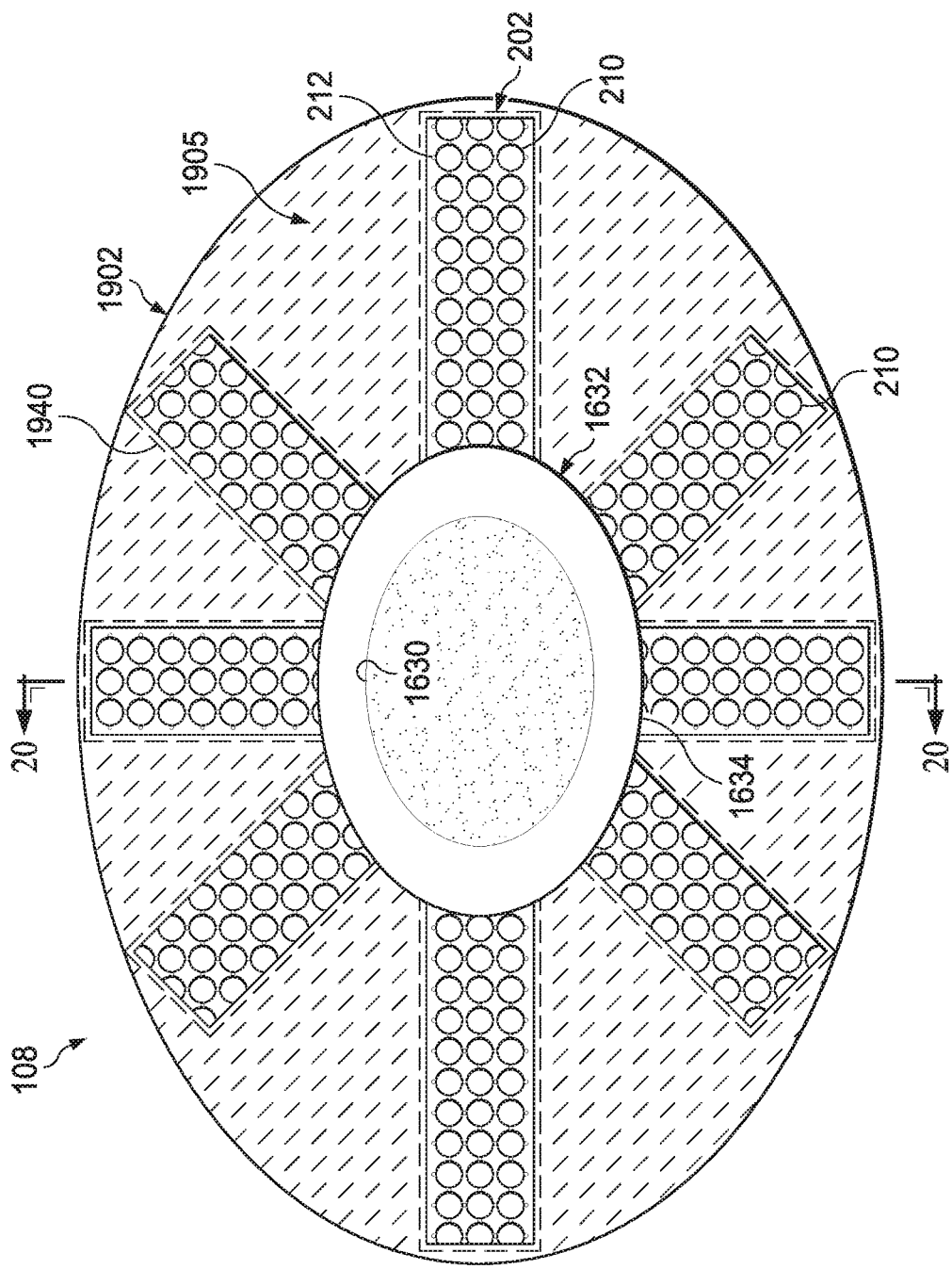
FIG. 19 is a schematic, plan view of another illustrative embodiment of a tissue interface that may be associated with some further embodiments of the therapy system of FIG. 1.

FIG. 19 is a schematic top-view of another example embodiment of a tissue interface 108, illustrating additional details that may be associated with some embodiments. The tissue interface 108 of FIG. 19 may comprise a manifold and may be adapted to provide negative pressure from the negative-pressure source 104 of the therapy system 100 to a tissue site, and to transport fluid extracted from the tissue site. The tissue interface 108 may comprise a fenestrated manifold 1902, a bubble manifold 202, and a foam manifold 1630. The fenestrated manifold 1902 may comprise a liquid-impermeable layer having fenestrations 1905.

The bubble manifold 202 may include a central portion and one or more fluid channels 1940, which may extend radially away from the central portion and may be configured to provide enhanced manifolding to the tissue interface 108. For example, the fluid channels 1940 of FIG. 19 may enhance the distribution of negative pressure from the negative-pressure source 104 of the therapy system 100 as well as enhance fluid removal capability of the tissue interface 108 when applied to a tissue site. Each of the fluid channels 1940 may comprise a plurality of bubbles 210, which may be in the form of open-celled blisters, spacers, protrusions, or closed cells. The width of each of the fluid channels 1940 may vary; however, in some instances, the fluid channels 1940 may be between about 2 cm and 15 cm in width. In some embodiments of the tissue interface 108 where the fluid channels 1940 include bubbles 210 comprising open-celled blisters, the bubble manifold 202 may be in the form of a single layer of liquid-impermeable material. In some embodiments, the bubble manifold 202 may be configured so that the bubbles 210 protrude or extend towards the fenestrated manifold 1902, while in other embodiments, the bubbles 210 may protrude or extend upwards or away from the fenestrated manifold 1902. The fluid channels 1940 may additionally comprise apertures 212 positioned between the bubbles 210 to allow fluid transfer through the bubble manifold 202 of the tissue interface 108.

The tissue interface 108 of FIG. 19 may also comprise foam manifold 1630, which may include a portion of manifolding or filler material positioned in a central portion of the tissue interface 108. For example, the tissue interface 108 may include a foam manifold 1630, which may be positioned adjacent a central portion of a surface of the bubble manifold 202 of the tissue interface 108. As shown in FIG. 19, the foam manifold 1630 may assume a circular or disc shape, as well as other possible shapes. Depending on the particular embodiment, the foam manifold 1630 may be positioned against a center region of the bubble manifold 202 that includes at least one film of liquid-impermeable material, which may or may not include bubbles in the center region. Similar to the previous embodiments discussed, the foam manifold 1630 may include one or more types of manifolding materials, such as an open-cell foam. The tissue interface 108 may further include a film 1632 positioned over the foam manifold 1630, and the foam manifold 1630 may be positioned between a surface of the bubble manifold 202 and the film 1632. The film 1632 may comprise any type of film material such as any suitable liquid-impermeable polymeric or drape materials, and may further include fenestrations. The film 1632 may be sealed around the foam manifold 1630 via a weld 1634 between the film 1632 and a surface of the bubble manifold 202 and/or fenestrated manifold 1902 surrounding a perimeter or circumference of the foam manifold 1630.

FIG. 20 is a section view of an example embodiment of the tissue interface 108 of FIG. 19, illustrating additional details that may be associated with some embodiments. In some embodiments, the tissue interface 108 may include a fenestrated manifold 1902, a bubble manifold 202, and a foam manifold 1630. The fenestrated manifold 1902 may comprise a liquid-impermeable layer having fenestrations 1905. The bubble manifold 202 of FIG. 20 may be formed from a plurality of liquid-impermeable layers. For example, the bubble manifold 202 may include a first layer of liquid-impermeable film, such as first layer 2002, and a second layer of liquid-impermeable film, such as second layer 2004. First layer 2002 and second layer 2004 may be sealingly coupled to one another in any suitable manner. As previously discussed with respect to other embodiments, the first layer 2002 and the second layer 2004 may comprise a non-adherent material, such as a breathable polyurethane film material. Each of the first layer 2002 and the second layer 2004 may include apertures, such as apertures 212, for allowing fluid transfer through the first layer 2002 and the second layer 2004 of the bubble manifold 202. The bubble manifold 202 of FIG. 20 may include one or more fluid channels 1940, which may be formed from portions of the first layer 2002 and the second layer 2004 that have been welded together to form the fluid channels 1940.

In some embodiments, the fluid channels 1940 may include a plurality of bubbles 210 comprising closed cells. For example, bubbles 210 comprising closed cells may extend along the length of each of the fluid channels 1940. The bubbles 210 may assist with communicating negative pressure to a tissue site and drawing fluids through the fluid channels 1940. For example, the bubbles 210 comprising closed cells may help maintain open fluid pathways through the fluid channels 1940 for receiving negative pressure from the negative-pressure source 104 and to distribute negative pressure through the multiple apertures 212 or perforations along the fluid channels 1940 and across a tissue site, which may have the effect of collecting fluids from across the tissue site and drawing the fluids toward the negative-pressure source 104.

The bubbles 210 comprising closed cells of the fluid channels 1940 may be formed by or between the first layer 2002 and the second layer 2004, and the closed cells may be filled with fluid such as air. Within the fluid channels 1940, each of the first layer 2002 and the second layer 2004 may comprise or consist essentially of a polymer film having inner surfaces coupled to each other to form one or more sealed regions. The bubbles 210 may be formed between the surface areas of the inner surfaces of the first layer 2002 and the second layer 2004 in the portions of the sealed regions defining the fluid channels 1940, and in this example embodiment, the bubbles 210 may be extending or protruding downwards as portions of the first layer 2002. The bubble manifold 202 may additionally include apertures 212 along the fluid channels 1940 through the first layer 2002 and the second layer 2004, and between the bubbles 210, to allow fluid transfer through the portions of the first layer 2002 and second layer 2004 forming the fluid channels 1940 of the bubble manifold 202. The fluid channels 1940 may provide enhanced manifolding or fluid transport capability along the surface of the first layer 2002 due to the presence of the bubbles 210 and associated spaces between the bubbles 210.

FIG. 21 shows a section view of another example embodiment of the tissue interface 108 of FIG. 19, illustrating additional details that may be associated with some embodiments. As shown in FIG. 21, in some alternative embodiments of the tissue interface 108 of FIG. 19, the fenestrated manifold 1902 may be omitted. In such embodiments, the bubble manifold 202 may instead include a layer of liquid-impermeable material defining the size and shape of the tissue interface 108. The single layer of liquid-impermeable material of the bubble manifold 202 may include regions comprising the fluid channels 1940 as well as regions of the liquid-impermeable layer between the fluid channels 1940, which may have fenestrations. In such embodiments, the bubbles 210 may be formed in the regions of the bubble manifold 202 comprising the fluid channels 1940, and the bubbles 210 may face downward away from the foam manifold 1630 and towards a bottom surface of the tissue interface 108 so as to be placed in contact with a tissue site. The bubbles 210 may comprise open-celled blisters. The fluid channels 1940 of the embodiment of the tissue interface 108 of FIG. 21 may provide substantially the same functionality as the fluid channels 1940 of FIG. 20.

Figure 22:
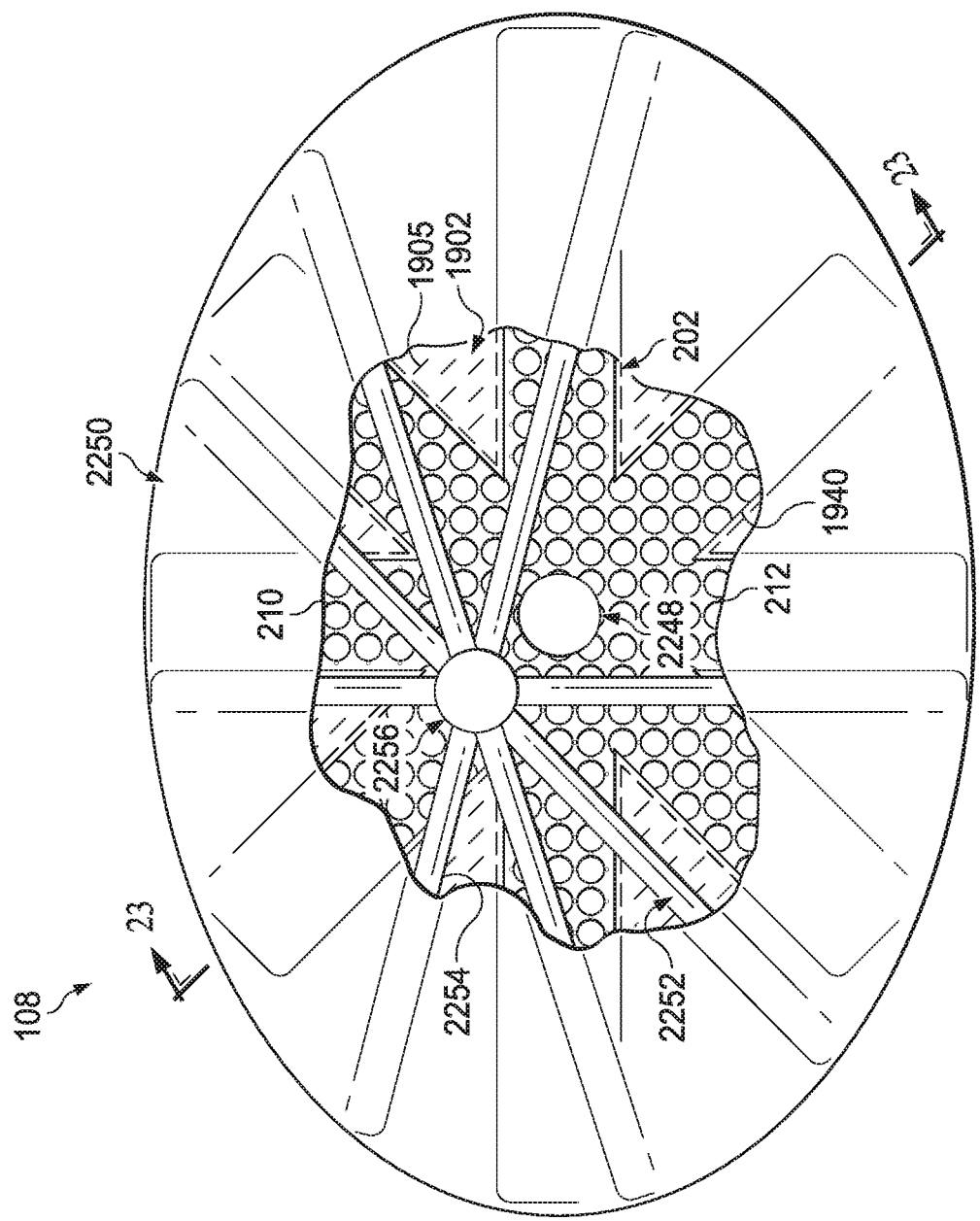
FIG. 22 is a schematic, cut-away plan view of another illustrative embodiment of a tissue interface that may be associated with some additional embodiments of the therapy system of FIG. 1.

FIG. 22 is a schematic cut-away view of another example embodiment of a tissue interface 108, illustrating additional details that may be associated with some embodiments. The tissue interface 108 of FIG. 22 may comprise a manifold and may be adapted to facilitate both fluid removal from a tissue site as well as delivery of treatment fluids to the tissue site. For example, the tissue interface 108 of FIG. 22 may be adapted to deliver negative pressure from the negative-pressure source 104 to a tissue site and to transport fluid extracted from the tissue site. The tissue interface 108 may also be adapted to deliver a fluid, such as a treatment fluid or medicament, from a fluid source, such as solution source 114 of therapy system 100, to the tissue site. The tissue interface 108 of FIG. 22 may comprise a fenestrated manifold 1902 and a bubble manifold 202. The fenestrated manifold 1902 may comprise a liquid-impermeable layer having fenestrations 1905.

The bubble manifold 202 may include one or more fluid channels 1940, which may be configured to provide enhanced manifolding to the tissue interface 108. Each of the fluid channels 1940 may comprise a plurality of bubbles 210, which may be in the form of open-celled blisters, spacers, protrusions, or closed cells. In some embodiments of the tissue interface 108 where the fluid channels 1940 include bubbles 210 comprising open-celled blisters, the bubble manifold 202 may be in the form of a single layer of liquid-impermeable material. For example, the bubbles 210 along the fluid channels 1940 may be open-celled blisters that may be extending downwards towards the fenestrated manifold 1902. Alternatively, the bubbles 210 may extend upwards, or away from the fenestrated manifold 1902. The fluid channels 1940 may additionally comprise apertures 212 positioned between the bubbles 210 to allow fluid transfer through the bubble manifold 202 of the tissue interface 108. Additionally, the tissue interface 108 may include a fluid removal hub 2248, which may be in fluid communication with each of the fluid channels 1940 and may serve as a distribution mechanism for communicating negative pressure to each of the fluid channels 1940 from the negative-pressure source 104 of the therapy system 100. Fluids, such as wound exudates, from the tissue site may be removed along or through the fluid channels 1940 and the fluid removal hub 2248.

In some additional embodiments, the fluid channels 1940 of the tissue interface 108 may include a plurality of bubbles 210 comprising closed cells, which may be positioned along the length of each of the fluid channels 1940. In such embodiments, the bubble manifold 202 may include both a first liquid-impermeable layer and a second liquid-impermeable layer, and the bubbles 210 comprising closed cells may be formed by or between the first and second layers of the bubble manifold 202. The closed cells may be filled with fluid such as air. Apertures 212 may be included along the fluid channels 1940 through the first and second layers of the bubble manifold 202 and between the bubbles 210 for allowing fluid transfer through the portions of the first and second layers of the bubble manifold 202 forming the fluid channels 1940.

The tissue interface 108 of FIG. 22 may also include a fluid distribution matrix 2252 for administering instillation fluid, such as from the solution source 114 of the therapy system 100, to a tissue site. The fluid distribution matrix 2252 may include a plurality of fluid delivery conduits 2254 and a fluid distribution hub 2256. The tissue interface 108 of FIG. 22 may further include an instillation layer 2250, which may comprise at least one additional liquid-impermeable film, which may comprise fenestrations, that is positioned above an upper surface of the bubble manifold 202, and may be coextensive with the fenestrated manifold 1902. The bubble manifold 202 may be positioned between the instillation layer 2250 and the fenestrated manifold 1902.

In some embodiments, the fluid delivery conduits 2254 may include segments of tubing or other material for forming fluid conduits. The components of the fluid distribution matrix 2252 may be constructed of a variety of different materials. For example, some or all of the components of the fluid distribution matrix 2252 may be constructed of soft, medical-grade silicone or PVC tubing material. The plurality of fluid delivery conduits 2254 may vary in size, based on the particular size and application of the tissue interface 108, as well as the conditions of a tissue site to which the tissue interface 108 may be applied. For example, the fluid delivery conduits 2254 may include segments of tubing forming fluid conduits, and the tubing may have an inner diameter of between 0.5 mm and 5 mm. In some further embodiments, the fluid delivery conduits 2254 may be formed by welding or otherwise adhering portions of the instillation layer 2250 to a surface of the fenestrated manifold 1902 to form channels.

FIG. 23 is a section view of an example embodiment of the tissue interface 108 of FIG. 22, illustrating some additional details that may be associated with some embodiments. In the example embodiment of FIG. 23, the tissue interface 108 may include a fenestrated manifold 1902 and a bubble manifold 202. The fenestrated manifold 1902 may comprise a liquid-impermeable layer having fenestrations 1905. The bubble manifold 202 may comprise a single layer of liquid-impermeable material and may include a plurality of bubbles 210 in the form of downward-facing open-celled blisters. In other embodiments, the bubble manifold 202 may include a first layer and a second layer that may be sealingly coupled to one another in any suitable manner to form bubbles comprising closed cells, and may include apertures. The bubble manifold 202 of FIG. 23 may include one or more fluid channels 1940, which may be formed from the layer of liquid-impermeable material. In other embodiments, the fluid channels may be formed from a first layer and a second layer of liquid-impermeable material that have been welded together to form the fluid channels 1940. Additionally, the tissue interface 108 of FIG. 23 may include a fluid distribution matrix 2252 and an instillation layer 2250.

In some embodiments, the fluid distribution matrix 2252 may be substantially encapsulated between the bubble manifold 202 and the instillation layer 2250. For example, the fluid distribution matrix 2252 may include fluid delivery conduits 2254, which may be positioned between the bubble manifold 202 and the instillation layer 2250. In some instances, the fluid distribution matrix 2252 may include additional tubing segments, as described above, which may be inserted between the bubble manifold 202 and the instillation layer 2250 at the time of manufacture, before the bubble manifold 202 and the instillation layer 2250 are attached or sealed together, for example by ultrasonic welding. In some embodiments, each of the fluid delivery conduits 2254 may be secured in place between the bubble manifold 202 and the instillation layer 2250 by welding the fenestrated manifold 1902, the bubble manifold 202, and the installation layer 2250 together along at least some of the borders of the fluid delivery conduits 2254 and/or fluid channels 1940. In some embodiments, the fluid delivery conduits 2254 may have open ends, such as conduit ends 2360, and may also have fluid openings along the lengths of the fluid delivery conduits 2254 for delivering instillation fluid to the tissue site. In some alternative embodiments, the fluid delivery conduits 2254 may have only open ends, such as conduit ends 2360, and may otherwise be fluidly isolated along the lengths of the fluid delivery conduits 2254. In some additional embodiments, the fluid delivery conduits 2254 may have fluid openings along the lengths of the fluid delivery conduits 2254, but may have closed ends. Regardless of configuration of the fluid delivery conduits 2254, the tissue interface 108 of FIGS. 22 and 23 may be cut, sized, and customized to reduce the size of the tissue interface 108, which may therefore reduce the lengths of the fluid delivery conduits 2254.

Continuing with FIG. 23, the fluid distribution hub 2256 may have a height that may allow the fluid distribution hub 2256 to extend from an outside surface of the tissue interface 108 through one or more layers of the tissue interface 108 and to be positioned in fluid communication with the fluid delivery conduits 2254. In some embodiments, the fluid distribution hub 2256 may extend outward from a surface of the instillation layer 2250 of the tissue interface 108, and at least a portion of the fluid distribution hub 2256 may be positioned between the bubble manifold 202 and the instillation layer 2250. The fluid distribution hub 2256 may include a first port on an upper surface, such as on the portion of the fluid distribution hub 2256 extending out from or above the instillation layer 2250, for receiving a fluid conduit, as well as a plurality of distribution ports positioned around the lower surface of the fluid distribution hub 2256. The distribution ports may be for fluidly coupling the fluid delivery conduits 2254 to the fluid distribution hub 2256. For example, the fluid delivery conduits 2254 may be positioned circumferentially about the fluid distribution hub 2256 and may extend radially away from the fluid distribution hub 2256 between the bubble manifold 202 and the instillation layer 2250. The fenestrated manifold 1902 of the tissue interface 108 may further include additional perforations through portions of the fenestrated manifold 1902 that may be aligned with the fluid delivery conduits 2254. The perforations may help facilitate the distribution of instillation fluids from the fluid delivery conduits 2254 to pass through the other layers of the tissue interface 108, such as the fenestrated manifold 1902, to a tissue site.

In some additional embodiments, a tissue interface that is suitable for both fluid removal and fluid instillation may include two or more layers of liquid-impermeable material, with at least one of the layers of liquid-impermeable material comprising bubbles. For example, as shown in FIG. 24A, a tissue interface 108 suitable for both fluid removal and fluid instillation may include a first layer 2402 comprising bubbles 210 in the form of open-celled blisters, and a second liquid-impermeable layer 2403. The first layer 2402 may further include a plurality of apertures 212. The second liquid-impermeable layer 2403 may be positioned adjacent to the first layer 2402 and may be laminated or welded to the first layer 2402. In some embodiments, the welds joining the second liquid-impermeable layer 2403 to the first layer 2402 may be positioned so as to define one or more fluid channels 2405 in a space between the second liquid-impermeable layer 2403 and the first layer 2402. A fluid removal hub 2448 may extend through holes in both of the second liquid-impermeable layer 2403 and the first layer 2402 to facilitate delivery of negative pressure and fluid removal. Additionally, the second liquid-impermeable layer 2403 may include an aperture 2407 for allowing a fluid delivery conduit to provide instillation fluid to the one or more fluid channels 2405 between the second liquid-impermeable layer 2403 and the first layer 2402.

In some further embodiments, a tissue interface suitable for both fluid removal and fluid instillation may include two or more layers of liquid-impermeable material comprising bubbles. For example, the tissue interface 108 of FIG. 2 may be doubled, tripled, or quadrupled, with the individual layers stacked on one another. Two instances of the tissue interface 108 of FIG. 2 may be laminated or welded together to provide for a fluid delivery layer and a separate fluid removal layer. In such embodiments, one or both of the bubble layers may include a hole to allow communication with the other layer as well as an underlying tissue site. For example, a hole through a first, or top, layer could be included to allow for a fluid delivery conduit to provide instillation fluid to the space between the two layers. Welds joining the two layers may be placed so as to define fluid channels between the two layers through which fluid may be instilled. Another set of holes could be made through both of the first and second layers, where the holes in each of the layers are aligned to allow for a fluid removal conduit to deliver negative pressure to the tissue site beneath both bubble layers. Such holes could be punch-formed after manufacture. Although not required, an additional piece of manifolding material, such as a foam, could be positioned against a central portion of the top layer of the tissue interface, and in some embodiments, fluid delivery and/or fluid removal conduits could have open ends that terminate against a top surface of the foam, or alternatively one or more of the conduits could pass through the foam to the bubble layers below the foam.

For example, as shown in FIG. 24B, a tissue interface 108 suitable for both fluid removal and fluid instillation may comprise four layers of liquid-impermeable material, with each of the four layers comprising bubbles. In some embodiments, the tissue interface 108 may include a first layer 2402, a second layer 2404, a third layer 2406, and a fourth layer 2408, and the four layers may be stacked on one another, with each of the four layers comprising bubbles 210 in the form of open-celled blisters. Each of the four liquid-impermeable layers may also include apertures 212 in order to allow fluid communication and manifolding through the layers. A first fluid pathway 2410 may be formed between the first layer 2402 and the second layer 2404 of the four layers, and may be suitable for communicating negative pressure. A second fluid pathway 2412 may be formed between the third layer 2406 and the fourth layer 2408, and may be suitable for delivering an instillation fluid. The bubbles 210 of each of the first layer 2402 and the second layer 2404 may protrude into the space between the first layer 2402 and the second layer 2404 defining the first fluid pathway 2410. Similarly, the bubbles 210 of each of the third layer 2406 and the fourth layer 2408 may protrude into the space between the third layer 2406 and the fourth layer 2408 defining the second fluid pathway 2412. A fluid removal hub 2448 may extend through the tissue interface 108 from a top surface of the tissue interface 108 to the first fluid pathway 2410 between the first layer 2402 and the second layer 2404 to facilitate delivery of negative pressure and fluid removal. A fluid distribution hub 2456 may extend from a top surface of the tissue interface 108 to the second fluid pathway 2412 between the third layer 2406 and the fourth layer 2408 to deliver instillation fluid. Portions of the four layers may be welded to each other, however at least portions of the peripheral edges of the four layers forming the tissue interface 108 may remain open so as to allow open pathways between the first fluid pathway 2410 and the second fluid pathway 2412 and the surrounding environment of a tissue site.

Figure 25:
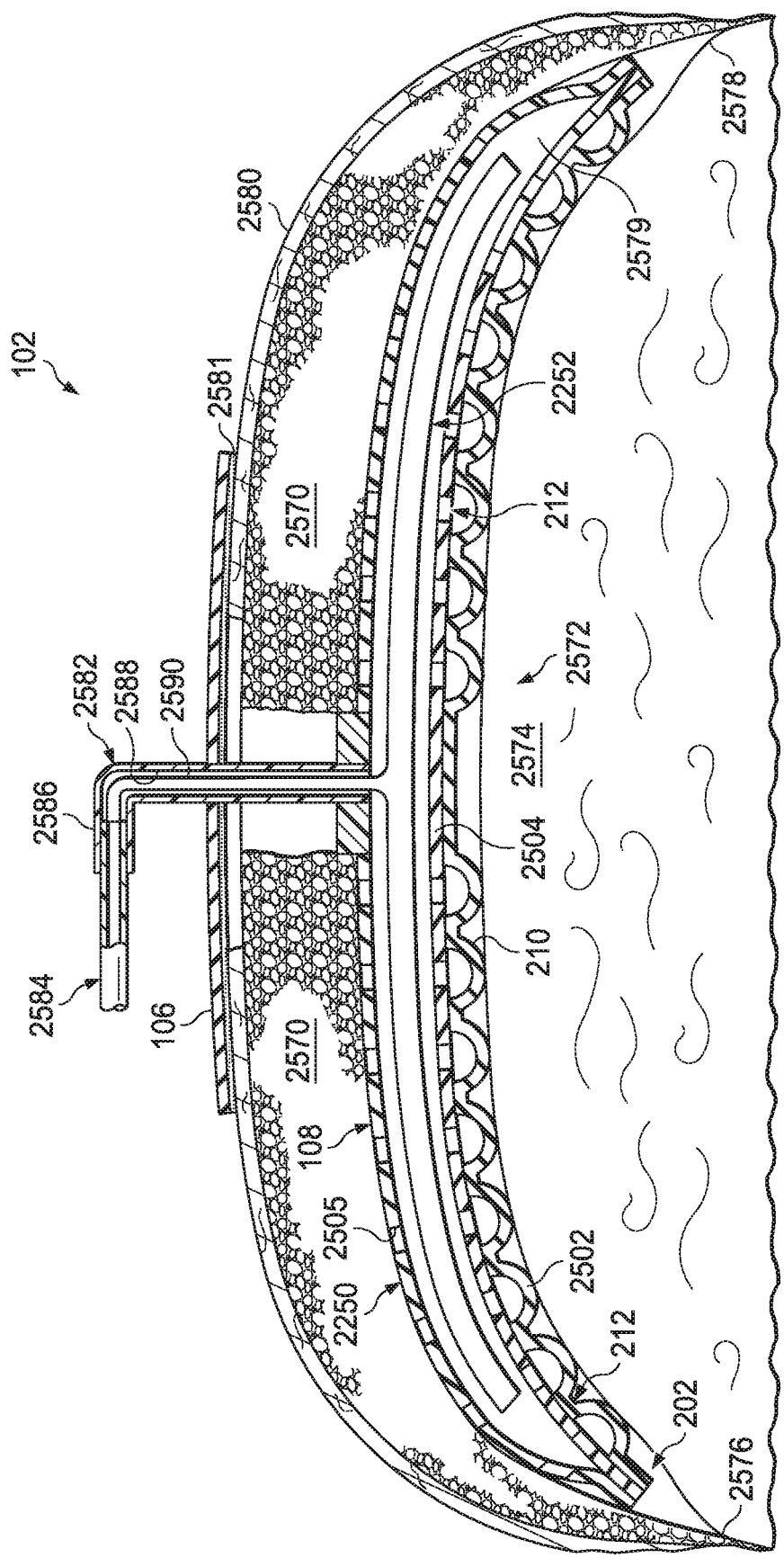
FIG. 25 is a schematic diagram, with a portion in cross-section, of an illustrative dressing for treating a tissue site, which may be associated with some embodiments of the therapy system of FIG. 1.

FIG. 25 is a schematic diagram illustrating additional details that may be associated with some example embodiments of the therapy system 100. More specifically, FIG. 25 shows a portion of an example embodiment of the dressing 102 for treating a tissue site 2572 within an abdominal cavity 2570. The tissue site 2572 may include the abdominal contents 2574 or tissue that is proximate the abdominal cavity 2570. Treatment of the tissue site 2572 may include removal of fluids, e.g., ascites, protection of the abdominal cavity 2570, or negative-pressure therapy.

As shown in FIG. 25, a dressing 102 may include a tissue interface 108, which may be disposed within the abdominal cavity 2570 of a patient to treat the tissue site 2572. The tissue interface 108 may be supported by the abdominal contents 2574. As depicted, the tissue interface 108 may extend throughout a portion of the abdominal cavity 2570, so that a portion of the tissue interface 108 is positioned in or proximate to a first paracolic gutter 2576, and another portion of the tissue interface 108 is positioned in or proximate to a second paracolic gutter 2578. The first paracolic gutter 2576 and the second paracolic gutter 2578 may each be, for example, an open space on opposing sides of the abdominal cavity 2570, among the abdominal contents 2574. The first paracolic gutter 2576 may be laterally disposed from the second paracolic gutter 2578 or otherwise positioned on an opposite side of the tissue site 2572 from the second paracolic gutter 2578. Although FIG. 25 depicts the dressing 102 deployed in the abdominal cavity 2570, the dressing 102 and therapy system 100 may be used at other types of tissue sites.

The example embodiment of the tissue interface 108 shown in FIG. 25 may allow for the instillation of a treatment fluid in addition to the delivery of negative pressure, and accordingly, the tissue interface 108 is shown as comprising both a bubble manifold 202 and an instillation layer 2250. As shown in FIG. 25, the bubble manifold 202 may include bubbles 210 comprising closed cells formed by two liquid-impermeable layers, the first layer 2502 and the second layer 25404. The installation layer 2250 may also comprise a liquid-impermeable layer. The plurality of liquid-impermeable layers of the bubble manifold 202 of FIG. 25, e.g., first layer 2502 and second layer 2504 may comprise apertures 212. Additionally, the instillation layer 2250 may have fenestrations 2505. The apertures 212 may take many shapes or combinations of shapes, including circular apertures or perforations, rectangular openings, fenestrations, or polygons, for example. The first layer 2502 may be adapted to be positioned between the second layer 2504 and the tissue site 2572 and abdominal contents 2574. The first layer 2502, second layer 2504, and the instillation layer 2250 may comprise a non-adherent material, such as a medical drape, capable of inhibiting tissue from adhering to the medical drape, such as a breathable polyurethane film. In the example embodiment of FIG. 25, a chamber 2579 is formed between the second layer 2504 and the instillation layer 2250. In some embodiments, the chamber 2579 formed between the second layer 2504 and the instillation layer 2250 may include a fluid distribution matrix 2252 for delivering instillation fluid to the tissue site 2572.

The dressing 102 may further include a cover, such as cover 106, for providing a fluid seal over the tissue site 2572 and the abdominal cavity 2570. Additionally, one or more skin closure devices may be placed on an epidermis 2580 of a patient. An attachment device, such as attachment device 2581, may be used to attach the cover 106 to an attachment surface, such as the epidermis 2580 of the patient. In some embodiments, the dressing 102 may also include an interface 2582 for fluidly connecting the tissue interface 108 and other portions of the dressing 102 to a conduit 2584. The interface 2582 may include a connector 2586. Alternatively, the interface 2582 may be partially or fully embedded with a portion of the dressing 102, or configured in any other way possible for fluidly connecting the tissue interface 108 to a negative-pressure source 104 and/or solution source 114. The conduit 2584 may be fluidly coupled to the negative-pressure source 104 and/or solution source 114 of the therapy system 100 for providing negative pressure and/or treatment fluid, respectively, to the tissue interface 108. In some embodiments, the conduit 2584 may include two substantially parallel, fluidly-isolated conduits, one of which may be for fluidly coupling the tissue interface 108 to the negative-pressure source 104 and the other for fluidly coupling the tissue interface 108 to the solution source 114. Thus, in some embodiments, the conduit 2584 may be a multi-lumen conduit with both a negative-pressure lumen 2588 and a fluid supply lumen 2590. In other example embodiments, the conduit 2584 may be replaced with two separate conduits, one containing a negative-pressure lumen and the other containing a fluid supply lumen.

Although not necessarily depicted in FIG. 25, in some embodiments, the dressing 102 may further include a filler material, such as a portion of a manifold material or foam, that is placed between the tissue interface 108 and the cover 106. The filler material may be sized to fill the portion of abdominal volume beneath or surrounding an incision or opening into the abdomen from the skin layers, such as a portion of the abdominal cavity 2570. In some embodiments, the filler material may serve as a distribution manifold for negative pressure. For example, in some embodiments, the filler material may be positioned between the tissue interface 108 and the cover 106, and a negative-pressure lumen or conduit, such as negative-pressure lumen 2588, may be pneumatically coupled to the cover 106. As a result, fluid removal may occur from the layers of the dressing 102, including the tissue interface 108, through the filler material positioned atop the tissue interface 108, and into the negative-pressure lumen 2588. In some embodiments, the filler material may include an open-cell, reticulated polyurethane foam such as GRANUFOAM™ Dressing or VERAFLOW™ Therapy foam, both available from Kinetic Concepts, Inc. of San Antonio, Tex. The filler material may alternatively or additionally include a three-dimensional woven or non-woven fabric, such as TDL2 or TDL4, commercially available from Libeltex of Meulebeke, Belgium, or 3DXD or 4DXD spacer fabrics, commercially available from Baltex of Derbyshire, England.

In some embodiments, one or more components of the dressing 102 may additionally be treated with an antimicrobial agent. For example, the first layer 2502, the second layer 2504, or the instillation layer 2250 of the tissue interface 108 may be coated with an antimicrobial agent. In some embodiments, the first layer 2502, the second layer 2504, and/or the instillation layer 2250 may comprise a polymer coated or mixed with an antimicrobial agent. In other examples, the cover 106, the interface 2582, the conduit 2584, or other portion of the dressing 102 may additionally or alternatively be treated with one or more antimicrobial agents. Suitable antimicrobial agents may include, for example, metallic silver, PHMB, iodine or its complexes and mixes such as povidone iodine, copper metal compounds, chlorhexidine, or some combination of these materials. In some embodiments, the hydrophilicity of one or more layers of the disclosed tissue interfaces, such as the tissue interface 108, may be further enhanced with a coating, such as by a plasma coating process used by P2i Limited of Oxfordshire, United Kingdom, of another material to make the layer(s) more or less hydrophilic, or oleo-phobic.

In use, the tissue interface 108 may be sized to fit a given tissue site, such as tissue site 2572 within the abdominal cavity 2570, and disposed at or within the tissue site. For example, the tissue interface 108 may be cut to remove excess portions to appropriately size the tissue interface 108 to fit a compartment such as the abdominal cavity 2570. In some embodiments of the tissue interface 108, excess portions may be removed by cutting or tearing the liquid-impermeable layers, such as the first layer 2502, the second layer 2504, and the instillation layer 2250, altogether, optionally using some of the apertures or fenestrations of the layers of the tissue interface 108 as a guide.

Still referring primarily to FIG. 25, the tissue interface 108 and other features of the dressing 102 may allow for the irrigation and washing out of an abdominal cavity, such as the abdominal cavity 2570, with the controlled and regulated introduction of fluid. In some instances, it may be necessary to wash or cleanse a contaminated abdominal cavity as a result of a perforated colon or sepsis. The therapy system 100 can provide means to instill fluid into an open abdomen to cleanse the abdominal contents, including reaching areas such as the small bowel loops, pancreas, etc. Additionally, the tissue interface 108 and other components of the dressing 102 and therapy system 100 may provide temporary closure to an open abdomen, while removing fluid and reducing edema. Thus, the therapy system 100 may provide the capability of performing washouts of a tissue site, such as abdominal cavity 2570, without having to repeatedly remove one or more dressings applied to the tissue site of a patient or brining the patient into the operating room for manual fluid introduction procedures. The therapy system 100 may thus be able to provide a controlled and regulated full abdominal wash, for example via instillation of a therapeutic fluid, as well as have the capability to provide a targeted wash to certain areas within the abdomen when required. Some embodiments of the therapy system 100, and more particularly the dressing 102, may also provide support and maintenance of the fascial domain of the abdominal cavity 2570, for example, and provide overall protection to the abdominal contents 2574.

Figure 26:
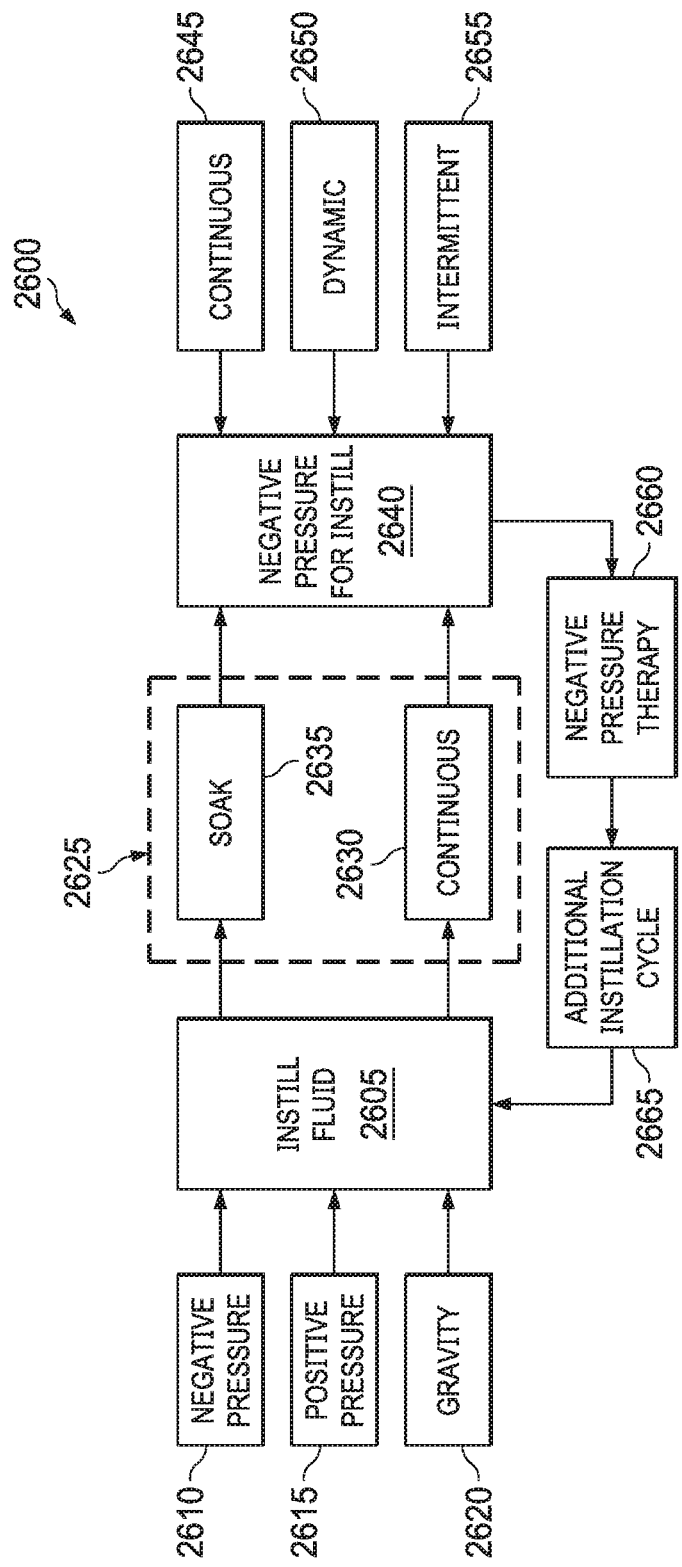
FIG. 26 is a chart illustrating details that may be associated with an example method of operating the therapy system of FIG. 1.

FIG. 26 is a chart illustrating details that may be associated with an example method 2600 of operating the therapy system 100 to provide negative-pressure treatment and instillation treatment to the tissue interface 108. In some embodiments, the controller 110 may receive and process data, such as data related to instillation solution provided to the tissue interface 108. Such data may include the type of instillation solution prescribed by a clinician, the volume of fluid or solution to be instilled to a tissue site ("fill volume"), and the amount of time prescribed for leaving solution at a tissue site ("dwell time") before applying a negative pressure to the tissue site. The fill volume may be, for example, between 10 and 500 mL, and the dwell time may be between one second and 30 minutes. The controller 110 may also control the operation of one or more components of the therapy system 100 to instill solution, as indicated at 2605.

For example, the controller 110 may manage fluid distributed from the solution source 114 to the tissue interface 108. In some embodiments, fluid may be instilled to a tissue site by applying a negative pressure from the negative-pressure source 104 to reduce the pressure at the tissue site, drawing solution into the tissue interface 108, as indicated at 2610. In some embodiments, solution may be instilled to a tissue site by applying a positive pressure from the positive-pressure source 116 to move solution from the solution source 114 to the tissue interface 108, as indicated at 2615. Additionally or alternatively, the solution source 114 may be elevated to a height sufficient to allow gravity to move solution into the tissue interface 108, as indicated at 2620.

The controller 110 may also control the fluid dynamics of instillation at 2625 by providing a continuous flow of solution at 2630 or an intermittent flow of solution at 2635. Negative pressure may be applied to provide either continuous flow or intermittent flow of solution at 2640. The application of negative pressure may be implemented to provide a continuous pressure mode of operation at 2645 to achieve a continuous flow rate of instillation solution through the tissue interface 108, or it may be implemented to provide a dynamic pressure mode of operation at 2650 to vary the flow rate of instillation solution through the tissue interface 108. Alternatively, the application of negative pressure may be implemented to provide an intermittent mode of operation at 2655 to allow instillation solution to dwell at the tissue interface 108. In an intermittent mode, a specific fill volume and dwell time may be provided depending, for example, on the type of tissue site being treated and the type of dressing being utilized. After or during instillation of solution, negative-pressure treatment may be applied at 2660. The controller 110 may be utilized to select a mode of operation and the duration of the negative pressure treatment before commencing another instillation cycle at 2665 by instilling more solution at 2605.

The systems, apparatuses, and methods described herein may provide significant advantages. For example, some embodiments of the tissue interface 108 may include fluid channels comprising bubbles, which may both assist with manifolding fluids and provide stiffness and/or structure to the tissue interface 108. For example, the inclusion of the bubbles as part of the tissue interface may provide good manifolding with a compressible, soft material that can conform to spaces and curves of a tissue site, such as a tissue site within an abdominal cavity. Additionally, the various layers and components of the tissue interface 108 may apply tension and closing force to the abdominal contents, therefore facilitating quicker primary fascia closure of the abdominal cavity. Some embodiments of the tissue interface 108 may reduce manufacturing cost. For example, bubbles in some embodiments of the tissue interface 108, when compressed under negative pressure in an abdominal cavity against a tissue site, may create conduits for transmission of negative pressure and fluid removal, without such conduits having to necessarily be constructed as separate structures into the tissue interface 108 during manufacturing. Additionally, some embodiments of the tissue interface 108 may allow for improved visibility of the underlying tissue site once applied.

Some embodiments of the tissue interface 108 may be incorporated as part of a dressing that is simple to apply, and can reduce the amount of time needed to size and apply the dressing. Furthermore, some embodiments of the tissue interface 108 disclosed herein may be cut and shaped without exposing foam or other materials that may allow in-growth of tissue and, thus, lead to disruption of the tissue site during dressing removal. Some embodiments of the tissue interface 108 may offer beneficial granulation and a low-trauma and high-seal bond with the tissue site, while substantially eliminating or minimizing incorporation with the tissue site. By incorporating manifolding elements comprising bubbles, such as the closed cells or blisters, possible tissue in-growth of the tissue site into portions of the tissue interface 108 within an abdominal cavity may be significantly reduced or eliminated. Longer application times for the tissue interface 108 and the dressing 102 without adhering to the fascia of abdominal tissue sites may be achieved. Some embodiments of the tissue interface 108 may remain in contact with a tissue site for longer periods of time without undergoing tissue in-growth, and as a result may maintain the ability to be easily removed. Since the tissue interface 108 may also have less mass than previous dressing materials, some embodiments of the tissue interface 108 may be removed through a smaller opening on a patient.

Some embodiments of the tissue interface 108 and dressing 102 may also provide combined temporary abdominal closure with fluid instillation capability. Such embodiments of the tissue interface 108 may therefore provide means for irrigating and cleansing an abdominal cavity while supporting and protecting the abdominal contents, as well as removing contaminated fluid and controlling and/or reducing edema. In some embodiments, the therapy system 100 may provide means for irrigating all areas of an abdominal cavity, including small bowel loops, gutters, retroperitoneal space, portions of the lymphatic system, etc., all while the dressing 102, including the tissue interface 108, is in place, advantageously reducing time required for patients and clinical staff in the operating room. Use of the therapy system 100 may enable exudate and infectious material to be drained from tissue sites, such as those within an abdominal cavity, which can reduce the presence of contaminated abdominal fluids, in order to promote healing. Furthermore, the therapy system 100 may provide separate instillation and negative-pressure pathways to ensure that contaminated fluid is fully removed from the tissue site. The tissue interface 108 may provide good interaction with tissue at a tissue site, including good manifolding of negative pressure and therapeutic fluids provided in conjunction with instillation therapy.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A system for treating an abdominal tissue site, comprising:
   a tissue interface comprising a liquid-impermeable layer and a plurality of bubbles, the liquid-impermeable layer comprising fenestrations positioned between the bubbles, the plurality of bubbles comprising closed cells containing a fluid;
   a fluid distribution matrix comprising a fluid distribution hub and a plurality of fluid distribution conduits fluidly coupled to a lower surface of the fluid distribution hub and extending radially away from the fluid distribution hub, the fluid distribution matrix for delivering instillation fluid to the abdominal tissue site;
   a cover adapted to form a fluid seal around the tissue interface and the abdominal tissue site; and
   a negative-pressure source adapted to be fluidly connected to the tissue interface;
   wherein the plurality of bubbles comprises:
      a first group of bubbles positioned in a central portion of the tissue interface,
         wherein each bubble of the first group of bubbles has a first diameter; and
      a second group of bubbles positioned in a peripheral portion of the tissue interface, wherein each bubble of the second group of bubbles has a second diameter;
      wherein the second diameter is greater than the first diameter.

2. The system of claim 1, wherein the liquid-impermeable layer of the tissue interface comprises a first sheet of polymeric film and a second sheet of polymeric film, wherein inner surfaces of each of the first sheet of polymeric film and the second sheet of polymeric film are sealed to each other to form a sealed region comprising the plurality of bubbles having closed cells.

3. The system of claim 2, wherein the closed cells are formed in the first sheet of polymeric film.

4. The system of claim 1, wherein the tissue interface further comprises a plurality of surface features comprising nodes, the plurality of surface features positioned on the plurality of bubbles.

5. The system of claim 1, wherein the tissue interface further comprises a foam manifold adapted to be positioned adjacent a central portion of the liquid-impermeable layer.

6. The system of claim 1, wherein:
   the first group of bubbles has a first spacing distance; and
   the second group of bubbles has a second spacing distance;
   wherein the second spacing distance is greater than the first spacing distance.

7. The system of claim 1, wherein a spacing distance between each of the plurality of bubbles increases along the tissue interface from the central portion to the perimeter of the tissue interface.

8. The system of claim 1, wherein a spacing distance between each of the plurality of bubbles decreases along the tissue interface from the central portion to the perimeter of the tissue interface.

9. A dressing for treating a tissue site, comprising:
   a first sheet of polymeric film comprising a first plurality of bubbles and a first plurality of apertures;

a second sheet of polymeric film comprising a second plurality of bubbles and a second plurality of apertures, the second sheet of polymeric film being substantially coextensive with the first sheet of polymeric film and forming a first fluid pathway between the first sheet of polymeric film and the second sheet of polymeric film;

a third sheet of polymeric film comprising a third plurality of bubbles and a third plurality of apertures, the third sheet of polymeric film being substantially coextensive with the first sheet of polymeric film;

a fourth sheet of polymeric film comprising a fourth plurality of bubbles and a fourth plurality of apertures, the fourth sheet of polymeric film being substantially coextensive with the first sheet of polymeric film and forming a second fluid passageway between the third sheet of polymeric film and the fourth sheet of polymeric film;

a fluid removal hub extending through the second sheet of polymeric film, the third sheet of polymeric film, and the fourth sheet of polymeric film, the first fluid removal hub adapted to deliver negative pressure to the first fluid pathway; and a fluid distribution hub extending through the fourth sheet of polymeric film, the fluid distribution hub adapted to deliver instillation fluid to the second fluid pathway;

wherein the first plurality of bubbles and the second plurality of bubbles are configured to protrude into the first fluid pathway and wherein the third plurality of bubbles and the fourth plurality of bubbles are configured to protrude into the second fluid pathway.

10. The dressing of claim 9, wherein the first plurality of bubbles and the second plurality of bubbles comprise open-celled blisters.

11. A system for treating a tissue site, comprising:

a fenestrated manifold comprising a first liquid-impermeable layer having a plurality of fenestrations, wherein the fenestrated manifold has a first side and a second side;

a bubble manifold comprising a second liquid-impermeable layer and a plurality of bubbles formed on the second liquid-impermeable layer, wherein the bubble manifold has a first side and a second side;

a fluid distribution matrix comprising a fluid distribution hub and a plurality of fluid distribution conduits fluidly coupled to a lower surface of the fluid distribution hub and extending radially away from the fluid distribution hub, the fluid distribution matrix for delivering instillation fluid to the tissue site;

wherein the plurality of bubbles comprises,
a first group of bubbles positioned in a central portion of the bubble manifold, wherein each bubble of the first group of bubbles has a first diameter; and
a second group of bubbles positioned in a peripheral portion of the bubble manifold, wherein each bubble of the second group of bubbles has a second diameter;
wherein the second diameter is greater than the first diameter.

12. The system of claim 11, wherein the bubble manifold is adapted to be positioned adjacent the fenestrated manifold such that the first side of the bubble manifold is in contact with the second side of the fenestrated manifold.

13. The system of claim 11, further comprising a fluid removal hub adapted to be in fluid communication with the bubble manifold.

14. The system of claim 11, wherein the plurality of bubbles comprises open-celled blisters.

15. The system of claim 11, wherein the plurality of bubbles comprises closed cells.

16. The system of claim 11, wherein the plurality of bubbles protrude from the first side of the bubble manifold and are adapted to be in contact with the second side of the fenestrated manifold.

17. The system of claim 11, wherein the bubble manifold comprises a a plurality of fluid channels that extend radially from the central portion of the bubble manifold.

18. The system of claim 11, further comprising a third liquid-impermeable layer adapted to be positioned adjacent the fluid distribution matrix and encapsulating the fluid distribution matrix between the fenestrated manifold and the third liquid-impermeable layer.

19. The system of claim 11, further comprising:
a negative-pressure source adapted to be in fluid communication with the fenestrated manifold and the bubble manifold; and
an interface adapted to fluidly couple the negative-pressure source to the fenestrated manifold and the bubble manifold.

* * * * *